United States Patent
David et al.

(10) Patent No.: US 10,662,161 B2
(45) Date of Patent: May 26, 2020

(54) PYRIMIDINES AND USES THEREOF

(71) Applicant: Regents of the University of Minnesota, Minneapolis, MN (US)

(72) Inventors: Sunil Abraham David, St. Paul, MN (US); Mallesh Beesu, Telangana (IN)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/879,826

(22) Filed: Jan. 25, 2018

(65) Prior Publication Data

US 2018/0215720 A1  Aug. 2, 2018

Related U.S. Application Data

(60) Provisional application No. 62/452,098, filed on Jan. 30, 2017.

(51) Int. Cl.

| | | |
|---|---|---|
| *C07D 239/47* | (2006.01) | |
| *C07D 239/48* | (2006.01) | |
| *C07D 239/49* | (2006.01) | |
| *C07D 239/50* | (2006.01) | |
| *A61K 31/506* | (2006.01) | |
| *A61K 31/505* | (2006.01) | |
| *A61P 37/06* | (2006.01) | |
| *C07D 403/06* | (2006.01) | |

(52) U.S. Cl.
CPC .......... *C07D 239/48* (2013.01); *A61K 31/505* (2013.01); *A61K 31/506* (2013.01); *A61P 37/06* (2018.01); *C07D 239/47* (2013.01); *C07D 239/49* (2013.01); *C07D 239/50* (2013.01); *C07D 403/06* (2013.01)

(58) Field of Classification Search
CPC .. C07D 239/48; C07D 239/47; C07D 239/49; C07D 239/50; C07D 403/06; C07D 2239/49; A61K 31/506; A61K 31/505; A61P 37/06
USPC .......................... 544/323, 324, 325; 514/275
See application file for complete search history.

(56) References Cited

U.S. PATENT DOCUMENTS

| | | | | |
|---|---|---|---|---|
| 6,458,798 B1 * | 10/2002 | Fujita | .................. | C07D 405/04 514/260.1 |
| 6,951,866 B2 * | 10/2005 | Fujita | .................. | C07D 405/04 514/275 |
| 9,284,304 B2 | 3/2016 | McGowan et al. | | |
| 2003/0105323 A1 * | 6/2003 | Fujita | .................. | C07D 405/04 544/323 |

OTHER PUBLICATIONS

Vippagunta et al., Advanced Drug Delivery Reviews 48: 3-26, 2001.*
Ulrich, Crystallization, Kirk-Othmer Encyclopedia of Chemical Technology, pp. 1-7, 2002.*
Chawla et al. CRIPS vol. 5, No. 1 Jan.-Mar. 2004, pp. 9-12.*
Beesu, Mallesh, et al., "Human Toll-like Receptor (TLR) 8-Specific Agonistic Activity in Substituted Pyrimidine-2,4-diamines", *Journal of Medicinal Chemistry*, 59(17), (2016), 8082-8093.
Beesu, Mallesh, et al., "Human Toll-like Receptor (TLR) 8-Specific Agonistic Activity in Substituted Pyrimidine-2,4-diamines", (Supporting Information), *Journal of Medicinal Chemistry*, 59(17), (2016), 70 pgs.
Beesu, Mallesh, et al., "Identification of High-Potency Human TLR8 and Dual TLR7/TLR8 Agonists in Pyrimidine-2,4-diamines", *Journal of Medicinal Chemistry*, 60(5), (2017), 2084-2098.
Beesu, Mallesh, et al., "Identification of High-Potency Human TLR8 and Dual TLR7/TLR8 Agonists in Pyrimidine-2,4-diamines", Supporting Information, *Journal of Medicinal Chemistry*, 60(5), (2017), 80 pgs.

* cited by examiner

*Primary Examiner* — Venkataraman Balasubramanian
(74) *Attorney, Agent, or Firm* — Schwegman Lundberg & Woessner, P.A.

(57) ABSTRACT

The various examples presented herein are directed to compounds of the Formula:

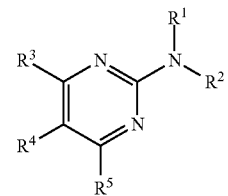

wherein $R^1$-$R^5$ are defined herein, and uses of such compounds to, among other things, inhibit an immune response in a subject.

10 Claims, 4 Drawing Sheets

PYRIMIDINES AND USES THEREOF

CROSS-REFERENCE TO RELATED APPLICATIONS

This application claims the benefit of priority from U.S. Provisional Appl. Ser. No. 62/452,098, filed Jan. 30, 2017, the entirety of which is incorporated by reference as if fully set forth herein.

STATEMENT OF GOVERNMENT SUPPORT

This invention was made with government support under grant HHSN272201400056C awarded by the National Institutes of Health/National Institute of Allergy and Infectious Diseases. The government has certain rights in the invention.

BACKGROUND OF THE INVENTION

Toll-like receptors (TLRs) are sensors in the activation of innate immune cells including monocytes, macrophages and dendritic cells. These cells function as sentinels against foreign antigens and pathogens, recognizing pathogen-associated molecular patterns (PAMPs) through pattern-recognition receptors (PRRs). Activation of PRRs initiate an array of innate immune responses, which serve to augment subsequent adaptive immune responses. The ten functional TLRs in the human encode proteins with an extracellular domain having leucine-rich repeats (LRR) and a cytosolic domain called the Toll/IL-1 receptor (TIR) domain. TLR1, -2, -4, -5, and -6 recognize extracellular stimuli, while TLR3, -7, -8 and -9 function within the endolysosomal compartment. The ligands for TLRs are highly conserved molecules such as lipopolysaccharides (LPS) and monophosphoryl lipid A (MPLA) (recognized by TLR4), lipopeptides (TLR2 in combination with TLR1 or TLR6), flagellin (TLR5), single stranded RNA (TLR7 and TLR8), double stranded RNA (TLR3), and CpG motif-containing DNA (recognized by TLR9).

T lymphocytes bear antigen specific receptors on their cell surface to allow recognition of foreign pathogens, and their effector functions are determined in part by the production of key cytokines. The two main subsets of T lymphocytes are distinguished by cell surface markers Cluster of Differentiation 4 (CD4) and CD8. CD4-expressing helper T lymphocytes are prolific cytokine producers and can be further subdivided into Th1 and Th2 subsets, depending on specific cytokine signatures. In the context of Th1-biased adaptive immune responses, TLR8 is of particular significance. The engagement of TLR8, which is expressed predominantly in myeloid dendritic cells, monocytes, and monocyte-derived dendritic cells, potently enhances the production of Th1-polarizing cytokines, tumor necrosis factor-α (TNF-α), interleukin-12 (IL-12), IL-18, and interferon-γ (IFN-γ).

BRIEF DESCRIPTION OF THE FIGURES

The drawings illustrate generally, by way of example, but not by way of limitation, various embodiments discussed in the present document.

DETAILED DESCRIPTION OF THE INVENTION

Introduction

Figure 1:
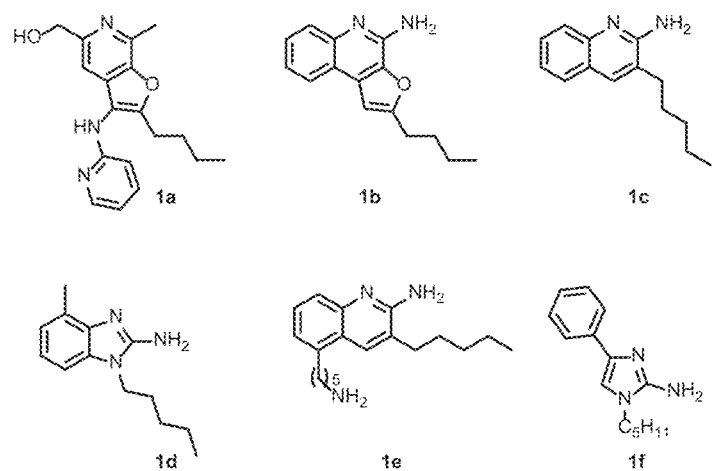
FIG. 1 is a diagram of several compounds identified in the primary screen from reporter gene assays.

Interest in Th1-polarizing small molecule agonists of TLR8 has led to the exploration of a variety of pure TLR8 agonists with no detectable activity at TLR7, including the 2,3-diamino-furo[2,3-c]pyridines,14 4-amino-furo[2,3-c]quinolines, 3-alkyl-quinoline-2-amines, 1-alkyl-2-aminobenzimidazoles, 2-amino-3-pentyl-5-alkylaminoquinolines, and the 2-aminoimidazoles.

Disclosed herein are substituted pyrimidines that are, among other things, Th1-polarizing small molecule agonists of TLR8. In some examples, the substituted pyrimidines disclosed herein have no detectable activity at TLR7. But in other examples, the substituted pyrimidines disclosed herein have dual TLR7/TLR8 activity. In some examples, dual TLR7/8 agonists activate multiple dendritic cell subsets, including pDCs, CD141+ cDCs, and CD1c+ cDCs.

The various compounds of the embodiments described herein are effective in a method of inhibiting an immune response in a subject (e.g., an animal subject, including a human), the method comprising administering to the subject an amount of the compounds of the various embodiments described herein, effective to inhibit the immune response in the subject. In some embodiments, the immune response is associated with an autoimmune disease. In some embodiments, inhibiting the immune response ameliorates one or more symptoms of the autoimmune disease. In some embodiments, the autoimmune disease is selected from the group consisting of rheumatoid arthritis, pancreatitis, mixed tissue connective disease, systemic lupus erythematosus, antiphospholipid syndrome, irritable bowel disease, type I diabetes mellitus, and Sjogren's disease.

Compounds

In some examples, the substituted pyrimidines have the Formula (I):

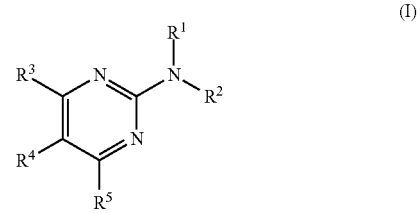

(I)

or a pharmaceutically acceptable salt, polymorph, prodrug, solvate or clathrate thereof, wherein:

$R^1$ and $R^2$ are each, independently, H, $(C_1-C_{20})$-alkyl or $(C_6-C_{20})$-aryl-$(C_1-C_{20})$-alkyl;

$R^3$ is $(C_1-C_{20})$-alkyl or $(C_6-C_{12})$-aryl;

$R^4$ is H, halo, $(C_6-C_{20})$-aryl-$(C_{1-20})$-alky or $(C_{1-20})$-alkyl-$NR^6R^7$, wherein $R^6$ and $R^7$ are each, independently, H, $(C_{1-20})$-alkyl or $(C_6-C_{20})$-aryl-$(C_{1-20})$-alkyl; and $R^5$ is $—NR^8R^9$, wherein $R^8$ and $R^9$ are each, independently, H, $(C_{1-20})$-alkyl or $(C_{6-12})$-aryl-$(C_{1-20})$-alkyl.

In some examples, $R^1$ and $R^2$ are each, independently, H, $(C_1-C_{20})$-alkyl or $(C_6-C_{20})$-aryl-$(C_1-C_{20})$-alkyl; $R^3$ is $(C_1-$ $C_{20}$)-alkyl or ($C_6$-$C_{12}$)-aryl; $R^4$ is ($C_1$-$C_{20}$)-alkyl, ($C_{1-20}$)-alkynyl, ($C_6$-$C_{20}$)-aryl-($C_{1-20}$)-alky, ($C_6$-$C_{20}$)-aryl-($C_{2-20}$)-alkynyl, ($C_6$-$C_{20}$)-cycloalkyl-($C_{1-20}$)-alkyl, ($C_{2-20}$)-alkynyl-$NR^6R^7$ or ($C_{1-20}$)-alkyl-$NR^6R^7$, wherein $R^6$ and $R^7$ are each, independently, H, ($C_{1-20}$)-alkyl, ($C_6$-$C_{20}$)-aryl-($C_{1-20}$)-alkyl or, $R^6$ and $R^7$, together with the nitrogen to which they are attached from a ($C_2$-$C_{20}$)-heterocyclyl group; and $R^5$ is —$NR^8R^9$, wherein $R^8$ and $R^9$ are each, independently, H, ($C_{1-20}$)-alkyl or ($C_{6-12}$)-aryl-($C_{1-20}$)-alkyl.

In some examples, in the compound of the Formula (I), $R^5$ is —$NR^8R^9$. In some examples, $R^8$ and $R^9$ are each, independently, H or ($C_{1-20}$)-alkyl.

In other examples, in the compound of the Formula (I), $R^3$ is ($C_1$-$C_6$)-alkyl. In still other examples, $R^3$ is ($C_1$-$C_6$)-alkyl and $R^4$ is halo or ($C_6$-$C_{20}$)-aryl-($C_{1-20}$)-alkyl. In yet other examples, $R^3$ is ($C_1$-$C_6$)-alkyl; $R^4$ is halo or ($C_6$-$C_{20}$)-aryl-($C_{1-20}$)-alkyl; and $R^5$ is —$NR^6R^7$.

In some examples, in the compound of the Formula (I), $R^4$ is ($C_{1-20}$)-alkyl-$NR^6R^7$. In other examples, $R^4$ is ($C_{1-20}$)-alkyl-$NR^6R^7$ and $R^3$ is ($C_1$-$C_6$)-alkyl. In still other examples, $R^4$ is ($C_{1-20}$)-alkyl-$NR^6R^7$; $R^3$ is ($C_1$-$C_6$)-alkyl; and $R^5$ is —$NR^8R^9$.

In some examples, in the compound of the Formula (I), $R^3$ is ($C_6$-$C_{12}$)-aryl. In other examples, $R^3$ is ($C_6$-$C_{12}$)-aryl and $R^4$ is ($C_{1-20}$)-alkyl-$NR^6R^7$. In still other examples, $R^3$ is ($C_6$-$C_{12}$)-aryl and $R^5$ is —$NR^8R^9$. In still other examples, $R^3$ is ($C_6$-$C_{12}$)-aryl; $R^4$ is ($C_{1-20}$)-alkyl-$NR^6R^7$; and $R^5$ is —$NR^8R^9$.

In some examples, the substituted pyrimidines have the Formula (II):

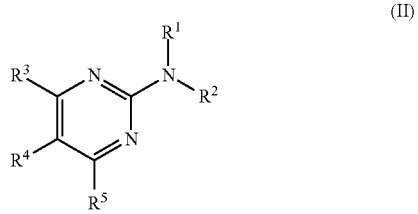

(II)

or a pharmaceutically acceptable salt, polymorph, prodrug, solvate or clathrate thereof, wherein:
$R^1$ and $R^2$ are each, independently, H, ($C_1$-$C_{20}$)-alkyl or ($C_6$-$C_{20}$)-aryl-($C_1$-$C_{20}$)-alkyl;
$R^3$ is ($C_1$-$C_{20}$)-alkyl or ($C_6$-$C_{12}$)-aryl;
$R^4$ is H, halo, ($C_1$-$C_{20}$)-alkyl, ($C_{1-20}$)-alkynyl, ($C_6$-$C_{20}$)-aryl-($C_{1-20}$)-alky, ($C_6$-$C_{20}$)-aryl-($C_{2-20}$)-alkynyl, ($C_6$-$C_{20}$)-cycloalkyl-($C_{1-20}$)-alkyl, ($C_{2-20}$)-alkynyl-$NR^6R^7$ or ($C_{1-20}$)-alkyl-$NR^6R^7$, wherein $R^6$ and $R^7$ are each, independently, H, ($C_{1-20}$)-alkyl, ($C_6$-$C_{20}$)-aryl-($C_{1-20}$)-alkyl or, $R^6$ and $R^7$, together with the nitrogen to which they are attached from a ($C_2$-$C_{20}$)-heterocyclyl group; and
$R^5$ is —$NR^8R^9$, wherein $R^8$ and $R^9$ are each, independently, H, ($C_{1-20}$)-alkyl or ($C_{6-12}$)-aryl-($C_{1-20}$)-alkyl.

In some examples, in the compound of the Formula (II), $R^4$ is ($C_{1-20}$)-alkyl-$NR^6R^7$, wherein $R^6$ and $R^7$ are each, independently, H, ($C_{1-20}$)-alkyl, ($C_6$-$C_{20}$)-aryl-($C_{1-20}$)-alkyl or, $R^6$ and $R^7$, together with the nitrogen to which they are attached from a ($C_2$-$C_{20}$)-heterocyclyl group. In some examples, $R^4$ is ($C_{1-20}$)-alkyl-$NR^6R^7$, wherein $R^6$ and $R^7$, together with the nitrogen to which they are attached from a ($C_2$-$C_{20}$)-heterocyclyl group. In some examples, the ($C_2$-$C_{20}$)-heterocyclyl group is a ($C_2$-$C_6$)-heterocyclyl group or a ($C_2$-$C_4$)-heterocyclyl group. Examples of suitable ($C_2$-$C_{20}$)-heterocyclyl groups include, but are not limited to:

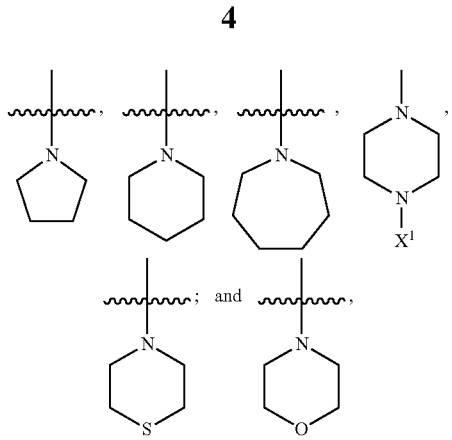

wherein $X^1$ represents H, ($C_1$-$C_{20}$)alkyl, ($C_6$-$C_{20}$)aryl or an amine protecting group (e.g., a t-butyloxycarbonyl group) and the heterocyclyl group can be substituted or unsubstituted.

In some examples, in the compound of the Formula (II), $R^3$ is ($C_1$-$C_{20}$)-alkyl (e.g., $C_1$-$C_6$)-alkyl); $R^4$ is ($C_{1-20}$)-alkyl-$NR^6R^7$, wherein $R^6$ and $R^7$ are each, independently, H, ($C_{1-20}$)-alkyl, ($C_6$-$C_{20}$)-aryl-($C_{1-20}$)-alkyl or, $R^6$ and $R^7$, together with the nitrogen to which they are attached from a ($C_2$-$C_{20}$)-heterocyclyl group; and $R^5$ is —$NR^8R^9$, wherein $R^8$ and $R^9$ are each, independently, H, ($C_{1-20}$)-alkyl (e.g., $C_1$-$C_6$)-alkyl) or ($C_{6-12}$)-aryl-($C_{1-20}$)-alkyl. In some examples, $R^4$ is ($C_{1-20}$)-alkyl-$NR^6R^7$, wherein $R^6$ and $R^7$, together with the nitrogen to which they are attached from a ($C_2$-$C_{20}$)-heterocyclyl group. In some examples, the ($C_2$-$C_{20}$)-heterocyclyl group is a ($C_2$-$C_6$)-heterocyclyl group or a ($C_2$-$C_4$)-heterocyclyl group. Examples of suitable ($C_2$-$C_{20}$)-heterocyclyl groups include, but are not limited to:

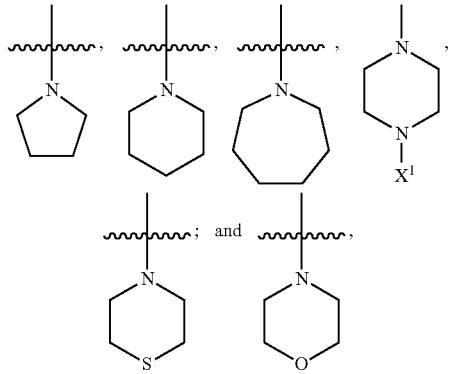

wherein $X^1$ represents H, ($C_1$-$C_{20}$)alkyl (e.g., $C_1$-$C_6$)-alkyl), ($C_6$-$C_{20}$)aryl or an amine protecting group (e.g., a t-butyloxycarbonyl group) and the heterocyclyl group can be substituted or unsubstituted.

Examples of compounds contemplated herein include compounds of the formulae:

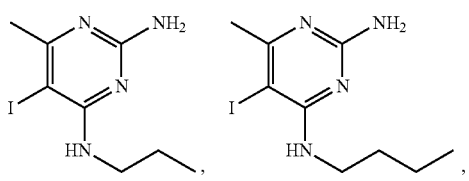

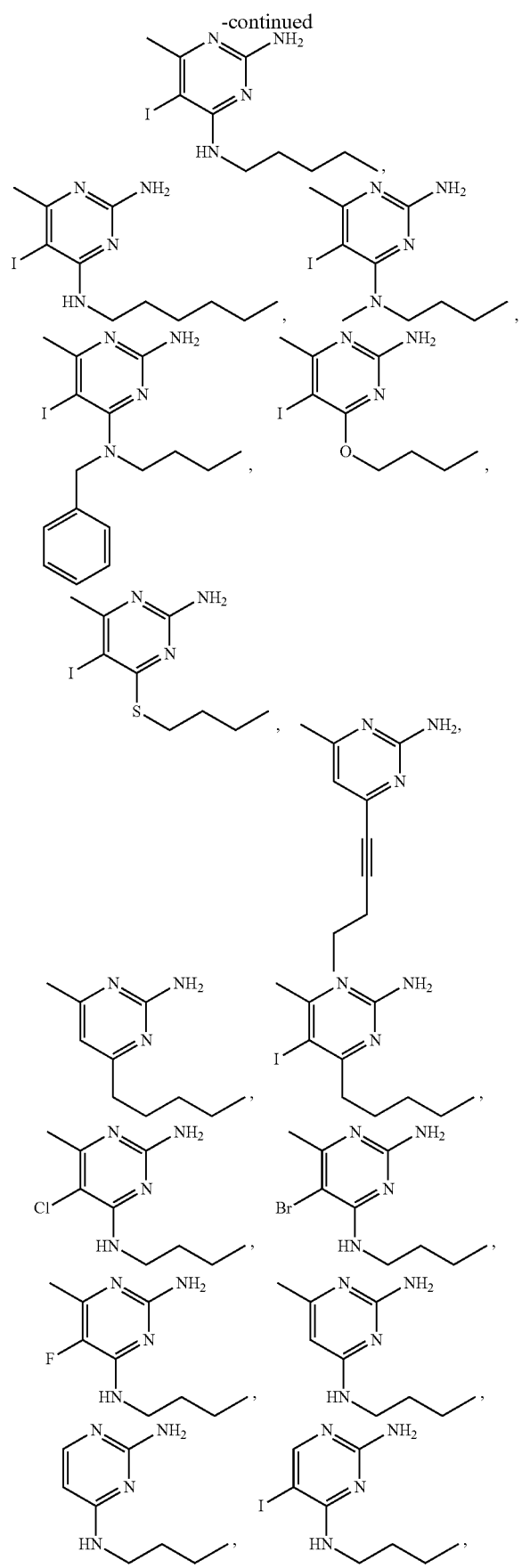
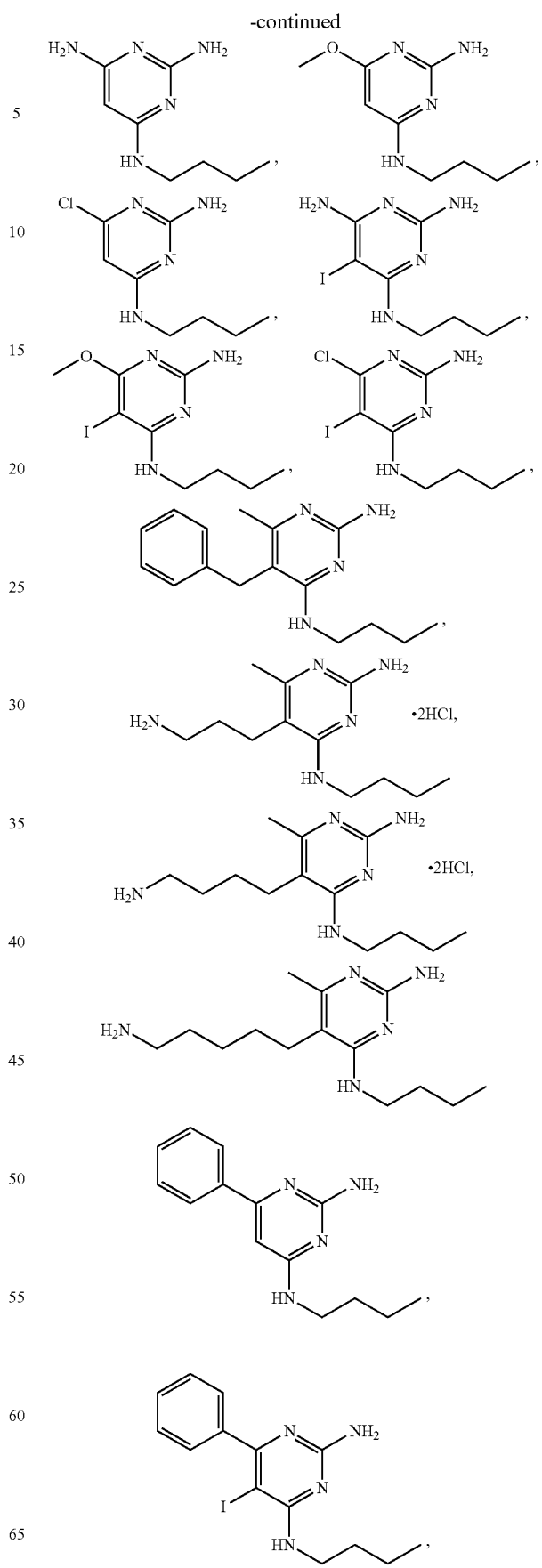

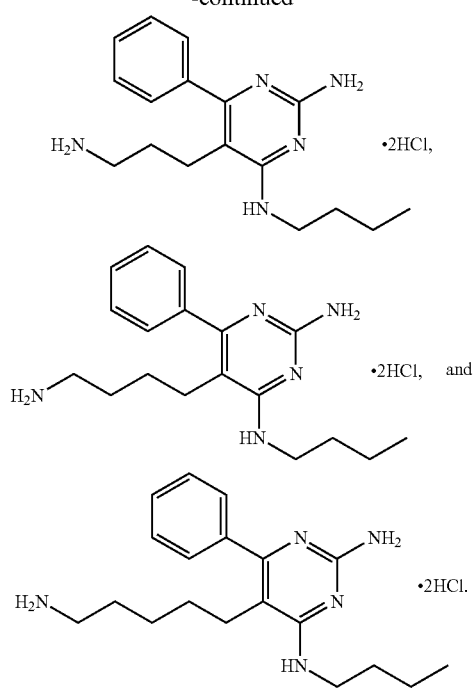
or pharmaceutically acceptable salts, polymorphs, prodrugs, solvates or clathrates thereof.
Examples of other compounds contemplated herein include compounds of the formulae:
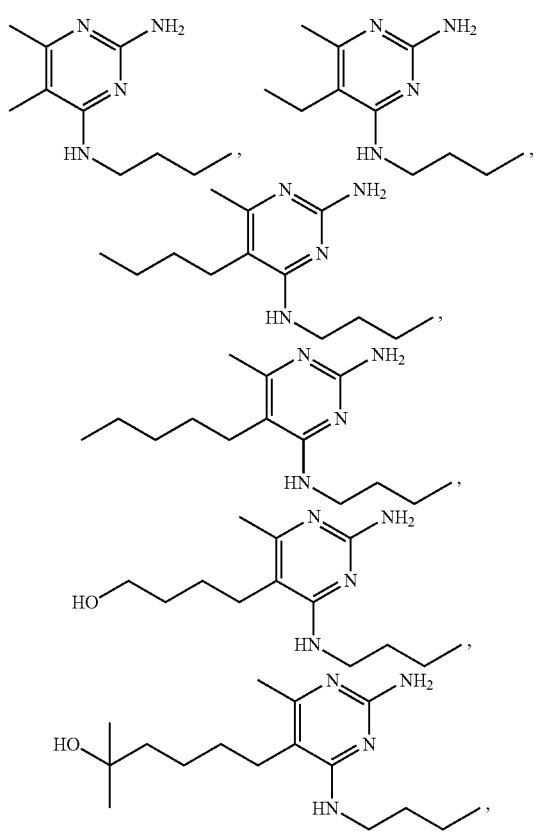
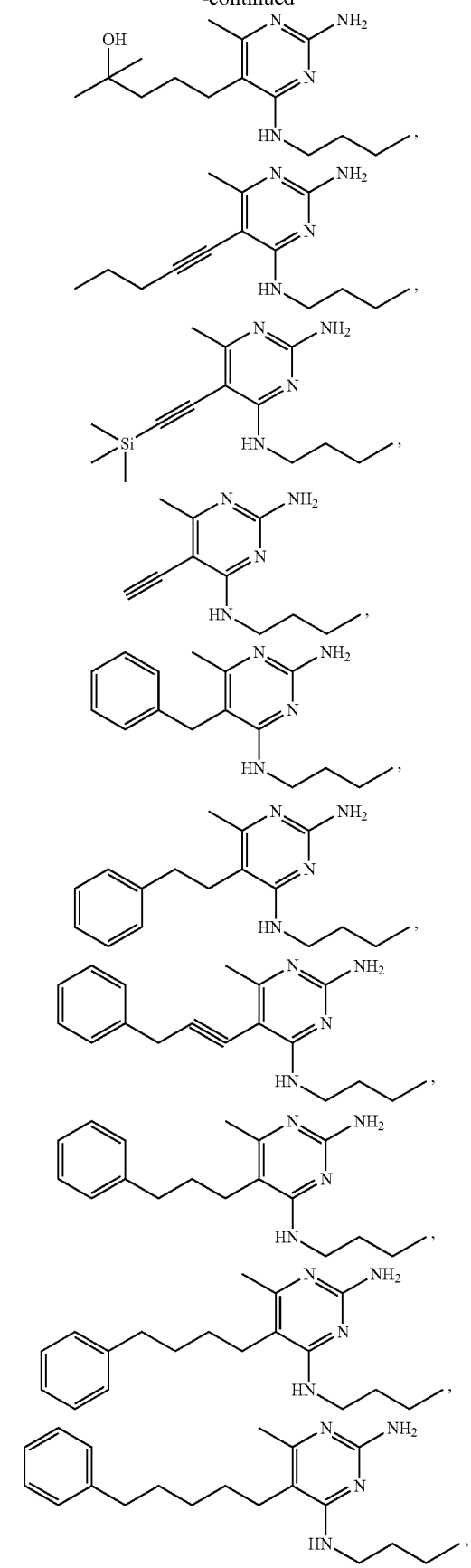

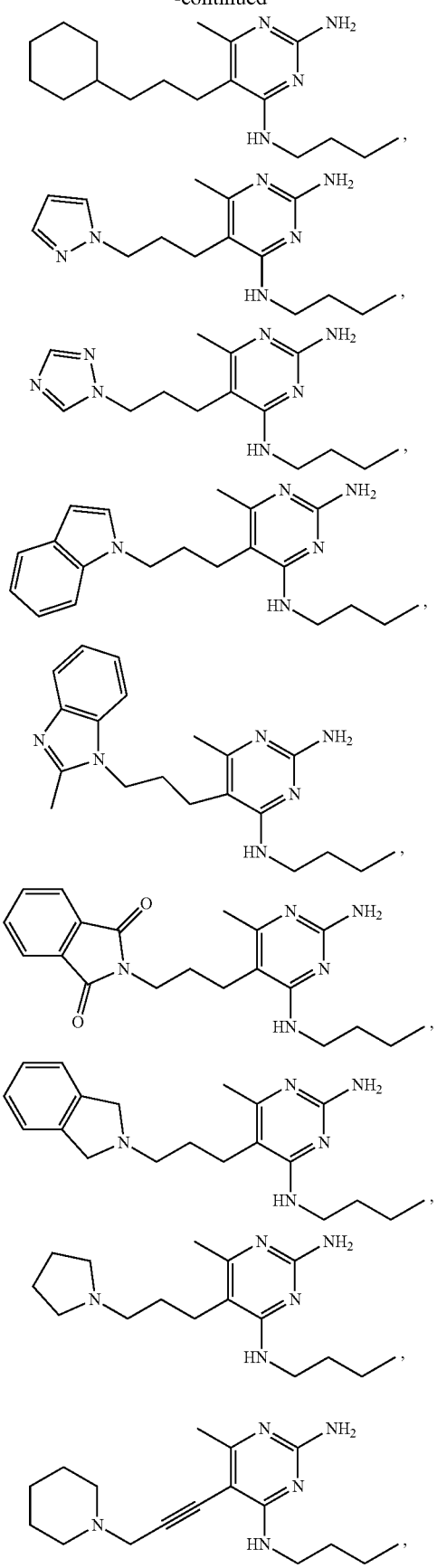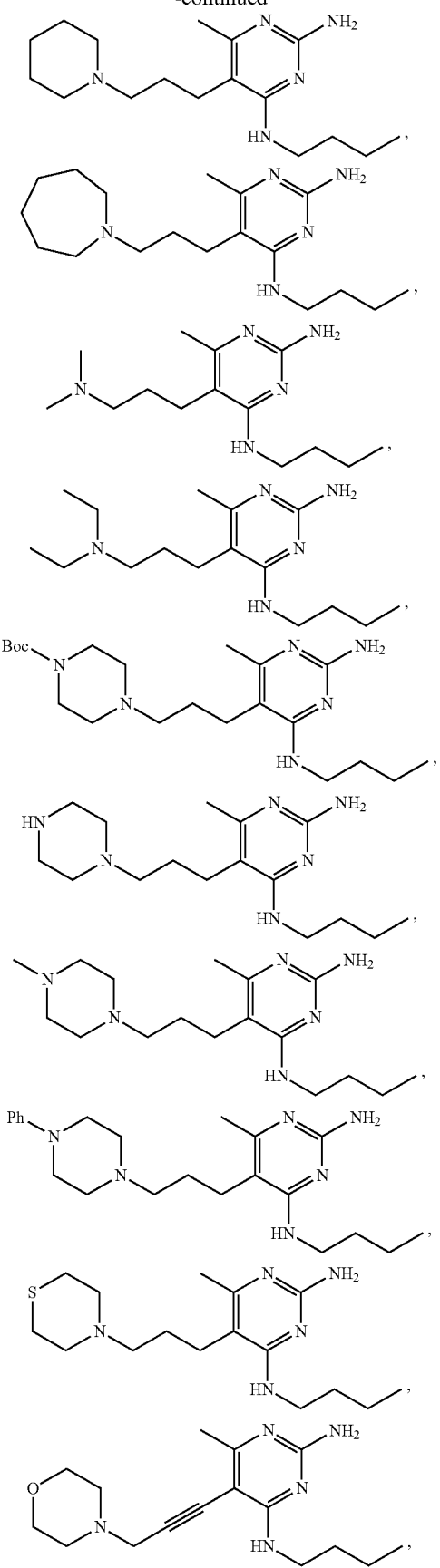

-continued

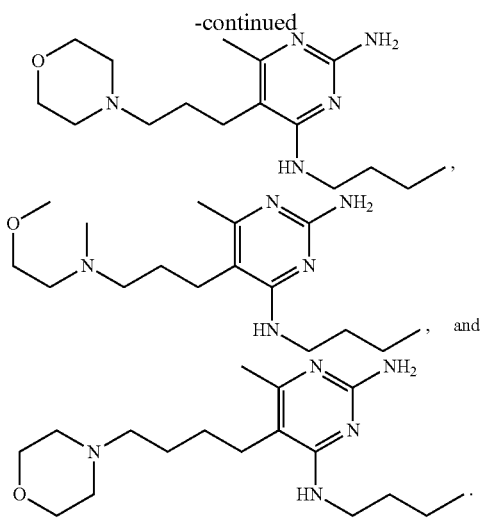

In some examples, compounds of the Formulae (I) and/or (II) exhibit TLR 8 agonisitc activity. In some examples, compounds of the Formulae (I) and/or (II) exhibit TLR 8 agonistic activity and no substantial TLR7 agonistic activity. In some examples, the compounds of the Formulae (I) and/or (II) have TLR8 agonisitic activity of from about 100 nM to about 100 μM (e.g., from about 100 nM to about 10 μM; about 100 nM to about 900 nM; about 250 nM to about 1 μM; or about 750 nM to about 100 μM).

In some examples, the compounds of the Formulae (I) and/or (II) have TLR8 agonisitic activity of from about 10 nM to about 100 μM (e.g., from about 100 nM to about 10 μM; about 100 nM to about 900 nM; about 250 nM to about 1 μM; about 1 μM to about 20 μM, about 10 nM to about 200 nm, or about 750 nM to about 100 μM). In some examples, the compounds of the Formulae (I) and/or (II) have TLR7 agonisitic activity of from about 30 nM to about 100 μM (e.g., from about 100 nM to about 10 μM; about 100 nM to about 900 nM; about 250 nM to about 1 μM; about 1 μM to about 20 μM, about 10 nM to about 200 nm, or about 750 nM to about 100 μM).

In some examples, the compounds of the Formulae (I) and/or (II) have TLR8 agonisitic activity of from about 10 nM to about 100 μM (e.g., from about 100 nM to about 10 μM; about 100 nM to about 900 nM; about 250 nM to about 1 μM; about 1 μM to about 20 μM, about 10 nM to about 200 nm, or about 750 nM to about 100 μM); and TLR7 agonisitic activity of from about 30 nM to about 100 μM (e.g., from about 100 nM to about 10 μM; about 100 nM to about 900 nM; about 250 nM to about 1 μM; about 1 μM to about 20 μM, about 10 nM to about 200 nm, or about 750 nM to about 100 μM).

Pharmaceutical Compositions

Various embodiments of the present invention also contemplate pharmaceutical compositions comprising one or more compounds of the various embodiments of the present invention and one or more pharmaceutically acceptable excipients. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" is a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes, but is not limited to, any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or lauryl-sulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the present invention may vary according to factors such as the disease state, age, gender, weight, patient history, risk factors, predisposition to disease, administration route, pre-existing treatment regime (e.g., possible interactions with other medications), and weight of the subject. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in subjects. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to, for example, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

Definitions

The term "$(C_1-C_{20})$alkyl" as used herein refers to substituted or unsubstituted straight chain and branched, saturated mono- or bi-valent groups having from 1 to 20 carbon atoms, 10 to 20 carbon atoms, 12 to 18 carbon atoms, 6 to about 10 carbon atoms, 1 to 10 carbons, 1 to 8 carbon atoms or 1 to 6 carbon atoms. Examples of straight chain monovalent $(C_1-C_{20})$-alkyl groups include those with from 1 to 8 carbon atoms such as methyl, ethyl, n-propyl, n-butyl, n-pentyl, n-hexyl, n-heptyl, n-octyl groups. Examples of branched mono-valent ($C_1$-$C_{20}$)-alkyl groups include iso-propyl, iso-butyl, sec-butyl, t-butyl, neopentyl, and isopentyl. Examples of straight chain bi-valent ($C_1$-$C_{20}$)alkyl groups include those with from 1 to 6 carbon atoms such as —$CH_2$—, —$CH_2CH_2$—, —$CH_2CH_2CH_2$—, —$CH_2CH_2CH_2CH_2$—, and —$CH_2CH_2CH_2CH_2CH_2$—. Examples of branched bi-valent ($C_1$-$C_{20}$)alkyl groups include —CH($CH_3$)$CH_2$— and —$CH_2$CH($CH_3$)$CH_2$—.

The term "($C_{2-20}$)-alkynyl" as used herein, refers to substituted or unsubstituted straight and branched chain alkyl groups, except that at least one triple bond exists between two carbon atoms. Thus, alkynyl groups have from 2 to 50 carbon atoms, 2 to about 20 carbon atoms, or from 2 to 12 carbons or, in some embodiments, from 2 to 8 carbon atoms. Examples include, but are not limited to —C≡CH, —C≡C($CH_3$), —C≡C($CH_2CH_3$), —$CH_2$C≡CH, —$CH_2$C≡C($CH_3$), and —$CH_2$C≡C($CH_2CH_3$) among others.

The term "($C_6$-$C_{20}$)aryl" as used herein refers to substituted or unsubstituted univalent groups that are derived by removing a hydrogen atom from an arene, which is a cyclic aromatic hydrocarbon, having from 6 to 20 carbon atoms, 10 to 20 carbon atoms, 12 to 20 carbon atoms, 6 to about 10 carbon atoms or 6 to 8 carbon atoms. Examples of ($C_6$-$C_{20}$) aryl groups include phenyl, napthalenyl, azulenyl, biphenylyl, indacenyl, fluorenyl, phenanthrenyl, triphenylenyl, pyrenyl, naphthacenyl, chrysenyl, anthracenyl groups. From these examples, it is clear that the term ($C_6$-$C_{20}$)aryl encompasses mono- and polycyclic ($C_6$-$C_{20}$)aryl groups, including fused and non-fused polycyclic ($C_6$-$C_{20}$)aryl groups.

The term "($C_2$-$C_{20}$)-heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_8$) or 6 to 8 carbon atoms ($C_6$-$C_8$). A heterocyclyl group designated as a $C_2$-heterocyclyl can be a 5-membered ring with two carbon atoms and three heteroatoms, a 6-membered ring with two carbon atoms and four heteroatoms and so forth. Likewise a $C_4$-heterocyclyl can be a 5-membered ring with one heteroatom, a 6-membered ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups. For example, heterocyclyl groups include:

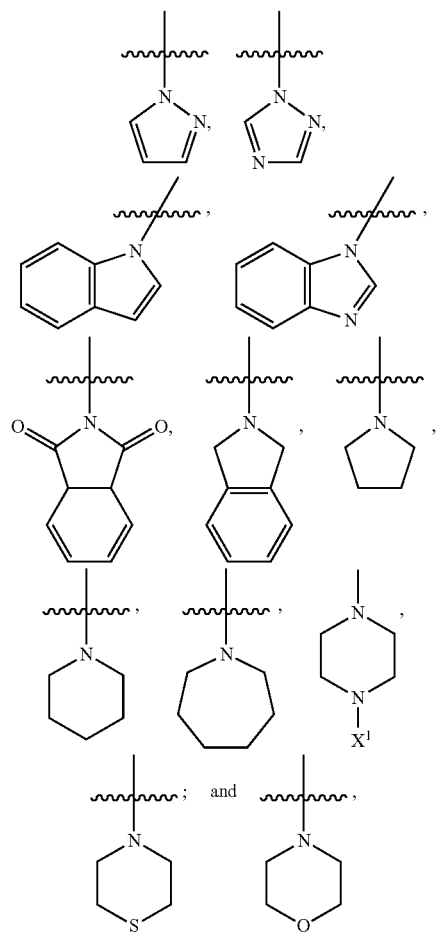

wherein $X^1$ represents H, ($C_1$-$C_{20}$)alkyl, ($C_6$-$C_{20}$)aryl or an amine protecting group (e.g., a t-butyloxycarbonyl group) and wherein the heterocyclyl group can be substituted or unsubstituted.

The term "substituted" as used herein refers to a group that is substituted with one or more groups including the following groups: halo (e.g., F, Cl, Br, and I), R, OR, OC(O)N(R)$_2$, CN, NO, NO$_2$, ONO$_2$, azido, CF$_3$, OCF$_3$, methylenedioxy, ethylenedioxy, ($C_3$-$C_{20}$)heteroaryl, N(R)$_2$, Si(R)$_3$, SR, SOR, SO$_2$R, SO$_2$N(R)$_2$, SO$_3$R, P(O)(OR)$_2$, OP(O)(OR)$_2$, C(O)R, C(O)C(O)R, C(O)CH$_2$C(O)R, C(S)R, C(O)OR, OC(O)R, C(O)N(R)$_2$, C(O)N(R)OH, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen, ($C_1$-$C_{20}$)alkyl or ($C_6$-$C_{20}$)aryl.

In some instances, the compounds described herein (e.g., the compounds of the Formulae (I) and (II)) can contain chiral centers. All diastereomers of the compounds described herein are contemplated herein, as well as racemates.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric (or larger) amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

As used herein, the term "subject" or "patient" refers to any organism to which a composition described herein may be administered, e.g., for experimental, diagnostic, prophylactic and/or therapeutic purposes. Subject refers to a mammal receiving the compositions disclosed herein or subject to disclosed methods. It is understood and herein contemplated that "mammal" includes but is not limited to humans, non-human primates, cows, horses, dogs, cats, mice, rats, rabbits, and guinea pigs.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carded out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "exhibits no substantial activity at TLR7" as used herein refers to less than 50%, less than about 40%, less than about 30%, less than about 20%, less than about 10%, less than about 5%, and less than about 1% activity at TLR7.

EXAMPLES

The present invention can be better understood by reference to the following examples which are offered by way of illustration. The present invention is not limited to the examples given herein.

Example 1

Compounds described herein can be synthesized according to the synthetic methods depicted in Schemes 1-4:

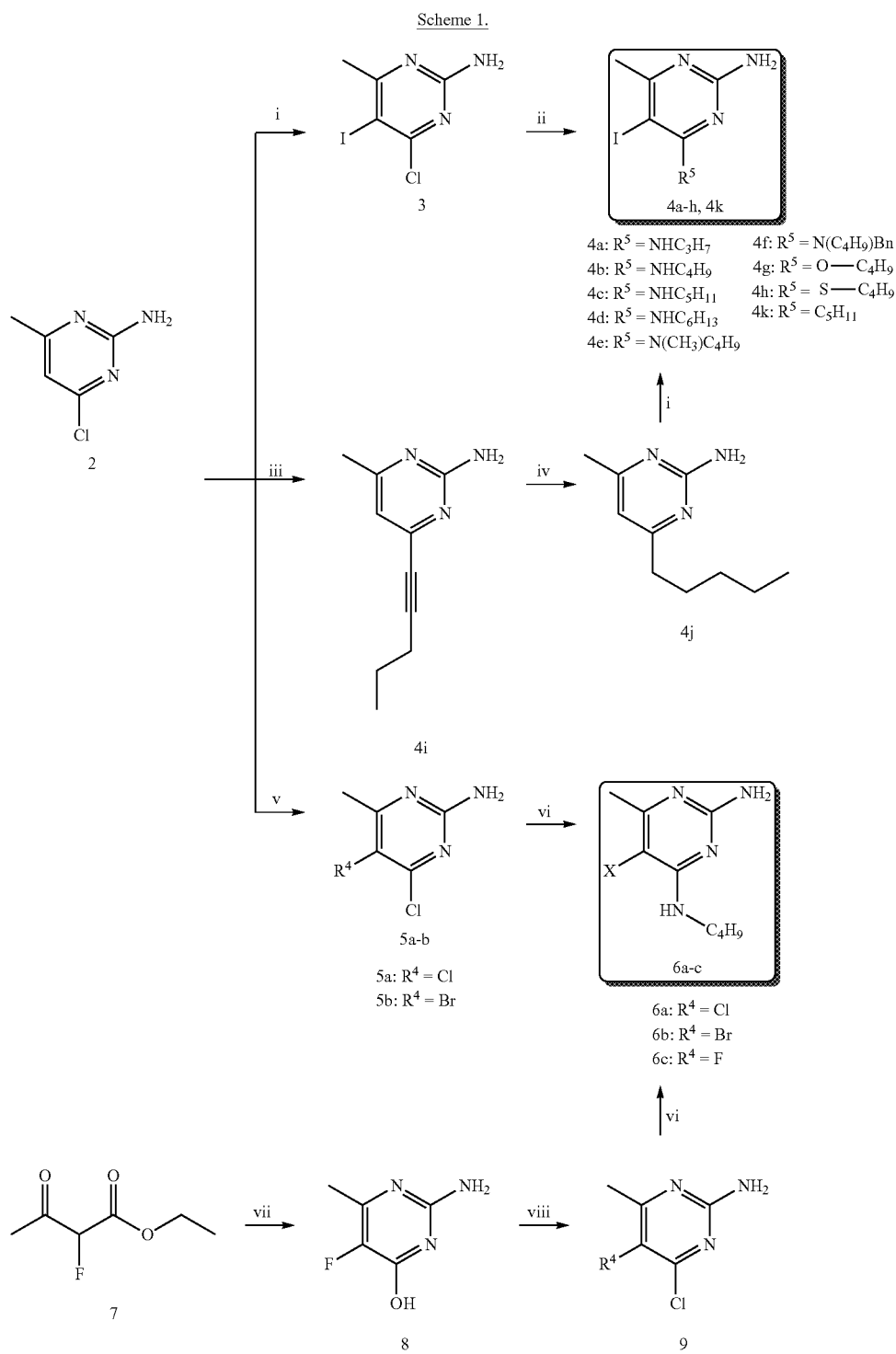

Reagents and conditions: (i) NIS, DMF, 12 h; (ii) alkylamine, Et$_3$N, MeOH, 70° C., 12 h (for 4a-f) or n-butanol, K$_2$CO$_3$ 85° C., 24 h (for 4g) or 1-butanethiol, Et$_3$N, MeOH, 70° C., 12 h (for 4h); (iii) 1-pentyne, Pd(pph$_3$)$_4$, CuI, Et$_3$N/CH$_3$CN (1:2), 12 h; (iv) Pd/C, EtOAc 50 psi, 5 h; (v) NCS (for 5a) or NBS (for 5b), DMF, 12 h; (vi) 5a (for 6a) or 5b (for 6b) or 9 (for 6c), butylamine, Et$_3$N, MeOH, 70° C. 12 h; (vii) guanidine hydrochloride, Et$_3$N, MeOH, reflux, 12 h; (viii) POCl$_3$, 85° C., 3 h.

Scheme 2.

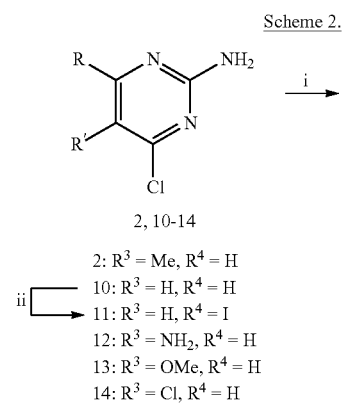

2, 10-14

2: $R^3$ = Me, $R^4$ = H
10: $R^3$ = H, $R^4$ = H
11: $R^3$ = H, $R^4$ = I
12: $R^3$ = NH$_2$, $R^4$ = H
13: $R^3$ = OMe, $R^4$ = H
14: $R^3$ = Cl, $R^4$ = H

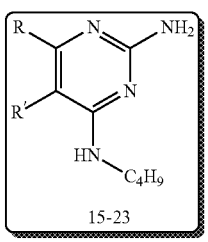

15-23

15: $R^3$ = Me, $R^4$ = H
16: $R^3$ = H, $R^4$ = H
17: $R^3$ = H, $R^4$ = I
18: $R^3$ = NH$_2$, $R^4$ = H
19: $R^3$ = OMe, $R^4$ = H
20: $R^3$ = Cl, $R^4$ = H
21: $R^3$ = NH$_2$, $R^4$ = I
22: $R^3$ = OMe, $R^4$ = I
23: $R^3$ = Cl, $R^4$ = I

-continued

Reagents and conditions: (i) Butylamine, Et$_3$N, MeOH, 70° C., 12 h; (ii) NIS, DMF, 12 h.

Scheme 3.

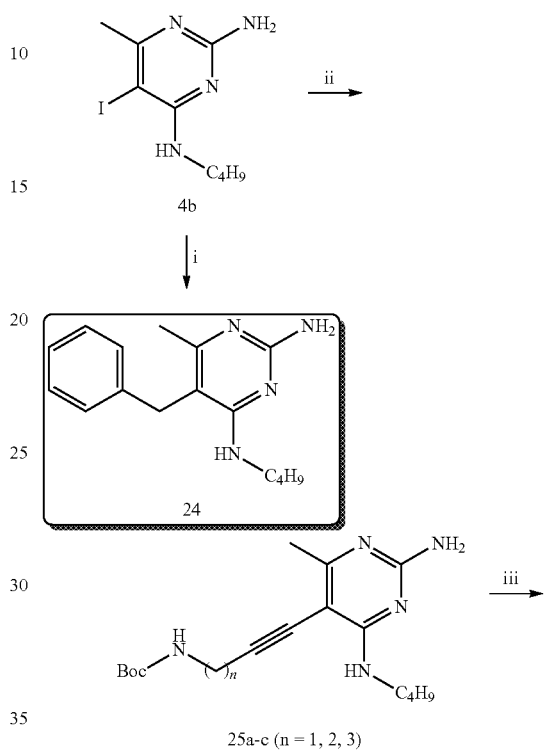

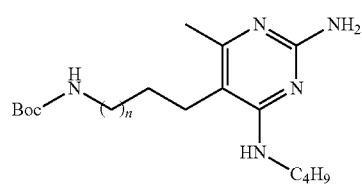

26a-c (n = 1, 2, 3)

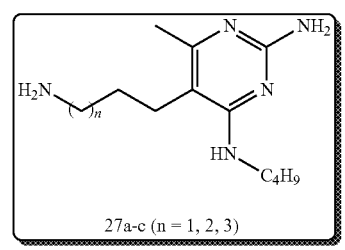

27a-c (n = 1, 2, 3)

Reagents and conditions: (i) Benzylboronic acid pinacol ester, Pd(dppf)Cl$_2$, K$_2$CO$_3$, 1,4-dioxane/water (4:1), 85° C., 12 h; (ii) N-boc-propargylamine (for 25a) or N-boc-3-butyne-1-amine (for 25b) or N-boc-4-pentyne-1-amine (for 25c), Pd(pph$_3$)$_4$, CuI, DIPEA/DMF (1:2), 12 h; (iii) Pd/C, EtOAc, 50 psi, 5 h; (iv) HCl, 4M, 3 h.

Scheme 4.

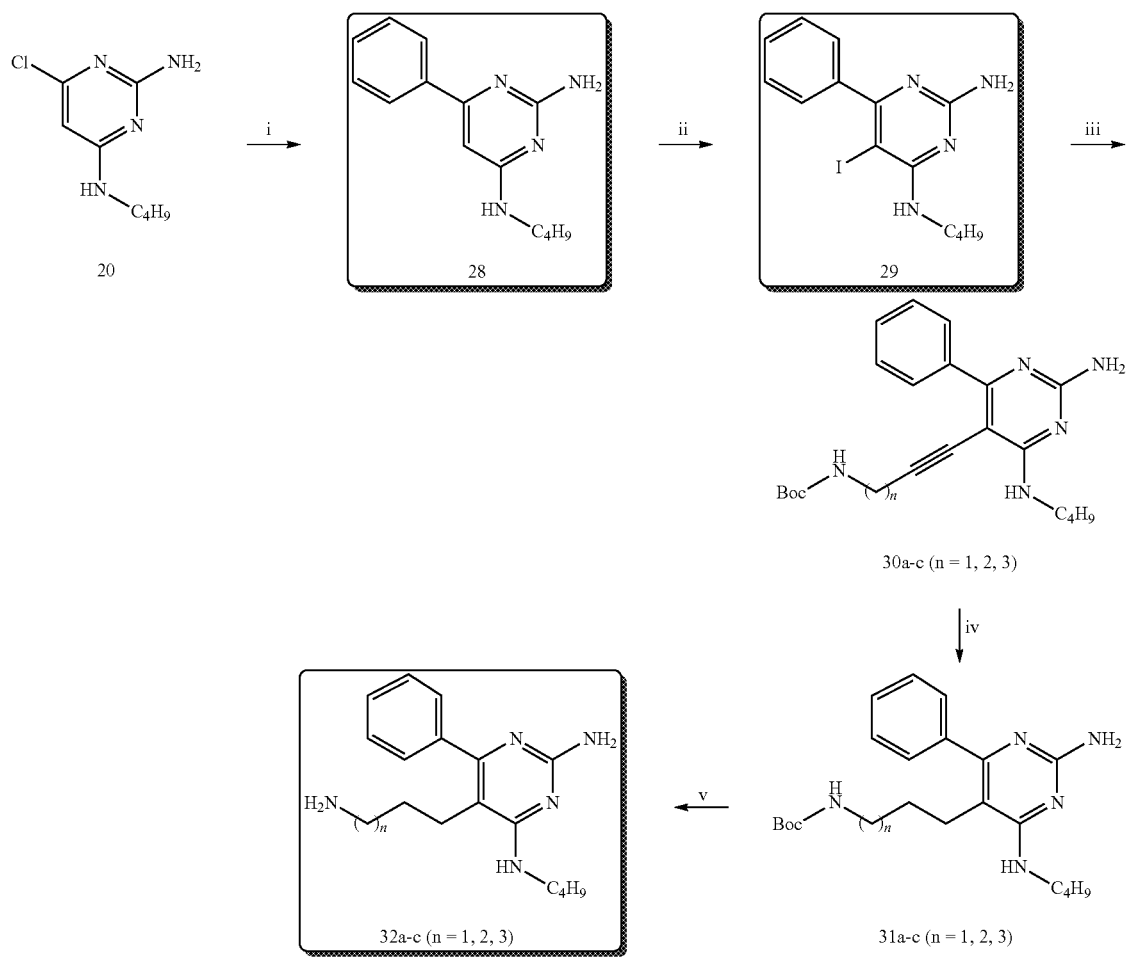

Reagents and conditions: (i) Phenylboronic acid, Pd(dppf)Cl₂, K₂CO₃, 1,4-dioxane/water (4:1), 85° C., 12 h; (ii) NIS, DMF, 12 h; (iii) N-boc-propargylamine (for 30a) or N-boc-3-butyne-1-amine (for 30b) or N-boc-4-pentyne-1-amine (for 30c), Pd(pph₃)₄, CuI, DIPEA/DMF (1:2), 12 h; (iv) Pd/C, EtOAc, 50 psi, 5 h; (v) HCl, 4M, 3 h.

All of the solvents and reagents used were obtained commercially and used as such unless noted otherwise. Moisture- or air-sensitive reactions were conducted under nitrogen atmosphere in oven-dried (120° C.) glass apparatus. Solvents were removed under reduced pressure using standard rotary evaporators. Flash column chromatography was carried out using RediSep Rf 'Gold' high performance silica columns on CombiFlash $R_f$ instruments unless otherwise mentioned; thin-layer chromatography was cardried out on silica gel CCM pre-coated aluminum sheets. Purity for all final compounds was confirmed to be greater than 98% by LC-MS using a Zorbax Eclipse Plus 4.6 mm×150 mm, 5 □m analytical reverse phase $C_{18}$ column with $H_2O$—$CH_3CN$ and $H_2O$—MeOH gradients and an Agilent 6520 ESI-QTOF Accurate Mass spectrometer (mass accuracy of 5 ppm) operating in the positive ion acquisition mode.

4-Chloro-5-iodo-6-methylpyrimidin-2-amine (3)

To a solution of compound 2 (143.6 mg, 1 mmol) in anhydrous DMF (5 mL) was added NIS (225 mg, 1 mmol), and the reaction mixture was stirred for 12 h. The reaction mixture was diluted with water and extracted with EtOAc (3×30 mL). The combined organic layer was dried over $Na_2SO_4$, concentrated under reduced pressure, and the crude material was purified by flash chromatography (40% EtOAc/hexanes) to obtain the compound 3 as a white solid (210 mg, 78%). $^1$H NMR (500 MHz, MeOD) δ 2.55 (s, 3H). $^{13}$C NMR (126 MHz, MeOD) δ 173.86, 165.51, 163.76, 79.58, 30.16. MS (ESI-TOF) for $C_5H_5ClIN_3$ [M+H]⁺ calculated 269.9289, found 269.9350.

$N^4$-Butyl-5-iodo-6-methylpyrimidine-2,4-diamine (4b)

To a solution of compound 3 (53.8 mg, 0.2 mmol) in MeOH (3 mL), was added Et₃N (56 µL, 0.4 mmol) and butylamine (39.5 µL, 0.4 mmol). The reaction mixture was stirred for 12 h at 70° C. The reaction mixture was cooled to room temperature and the solvent was removed under reduced pressure. The reaction mixture was diluted with water and extracted with EtOAc (3×20 mL). The combined organic layer was dried over $Na_2SO_4$ and concentrated under reduced pressure, and the crude material was purified by flash chromatography (70% EtOAc/hexanes) to afford the compound 4b as a white solid (46 mg, 75%). $^1$H NMR (500

MHz, CDCl$_3$) δ 5.24 (s, 1H), 4.76 (s, 2H), 3.42-3.34 (m, 2H), 2.40 (s, 3H), 1.63-1.53 (m, 2H), 1.44-1.34 (m, 2H), 0.95 (t, J=7.4 Hz, 3H). $^{13}$C NMR (126 MHz, CDCl$_3$) δ 166.52, 162.16, 161.04, 68.50, 41.59, 31.65, 28.84, 20.26, 13.99. MS (ESI-TOF) for C$_9$H$_{15}$IN$_4$ [M+H]$^+$ calculated 307.0414, found 307.0408.

Compounds 4a and 4c-f were synthesized similarly as compound 4b.

5-iodo-6-methyl-M-propylpyrimidine-2,4-diamine (4a)

Propylamine was used as reagent. White solid (40 mg, 68%). $^1$H NMR (500 MHz, CDCl$_3$) δ 5.27 (s, 1H), 4.78 (s, 2H), 3.39-3.31 (m, 2H), 2.40 (s, 3H), 1.67-1.56 (m, 2H), 0.97 (t, J=7.4 Hz, 3H). $^{13}$C NMR (126 MHz, CDCl$_3$) δ 166.55, 162.18, 161.05, 68.47, 43.57, 28.84, 22.77, 11.56. MS (ESI-TOF) for C$_8$H$_3$IN$_4$ [M+H]$^+$ calculated 293.0258, found 293.0249.

5-iodo-6-methyl-N$^4$-pentylpyrimidine-2,4-diamine (4c)

Amylamine was used as reagent. White solid (55 mg, 86%). $^1$H NMR (500 MHz, CDCl$_3$) δ 5.24 (s, 1H), 4.67 (s, 2H), 3.42-3.34 (m, 2H), 2.41 (s, 3H), 1.65-1.55 (m, 2H), 1.41-1.31 (m, 4H), 0.92 (t, J=6.7 Hz, 3H). $^{13}$C NMR (126 MHz, CDCl$_3$) 166.66, 162.21, 161.05, 68.58, 41.87, 29.26, 29.25, 28.91, 22.56, 14.18. MS (ESI-TOF) for C$_{10}$H$_{17}$IN$_4$ [M+H]$^+$ calculated 321.0571, found 321.0566.

N$^4$-Hexyl-5-iodo-6-methylpyrimidine-2,4-diamine (4d)

Hexylamine was used as reagent. White solid (56 mg, 84%). $^1$H NMR (500 MHz, CDCl$_3$) δ 5.25 (s, 1H), 4.76 (s, 2H), 3.41-3.33 (m, 2H), 2.41 (s, 3H), 1.63-1.54 (m, 2H), 1.40-1.29 (m, 6H), 0.89 (t, J=6.6 Hz, 3H). $^{13}$C NMR (126 MHz, CDCl$_3$) δ 166.51, 162.16, 161.03, 68.51, 41.89, 31.65, 29.49, 28.84, 26.74, 22.72, 14.18. MS (ESI-TOF) for C$_{11}$H$_{19}$IN$_4$ [M+H]$^+$ calculated 335.0727, found 335.0895.

N$^4$-Butyl-5-iodo-N$^4$,6-dimethylpyrimidine-2,4-diamine (4e)

N-Methyl-1-butanamine was used as reagent. White solid (46 mg, 72%). $^1$H NMR (500 MHz, CDCl$_3$) δ 4.73 (s, 2H), 3.38 (t, J=7.5 Hz, 2H), 2.98 (s, 3H), 2.50 (s, 3H), 1.68-1.58 (m, 2H), 1.37-1.25 (m, 2H), 0.93 (t, J=7.4 Hz, 3H). $^{13}$C NMR (126 MHz, CDCl$_3$) δ 170.11, 167.82, 161.10, 68.63, 53.08, 39.65, 30.36, 29.78, 20.23, 14.09. MS (ESI-TOF) for C$_{10}$H$_{17}$IN$_4$ [M+H]$^+$ calculated 321.0571, found 321.0593.

N$^4$-Benzyl-N$^4$-butyl-5-iodo-6-methylpyrimidine-2,4-diamine (4f)

N-Benzyl-n-butylamine was used as reagent. White solid (62 mg, 78%). $^1$H NMR (500 MHz, CDCl$_3$) δ 7.32-7.29 (m, 4H), 7.26-7.21 (m, 1H), 4.75 (s, 2H), 4.63 (s, 2H), 3.34 (t, J=7.5 Hz, 2H), 2.53 (s, 3H), 1.62-1.51 (m, 2H), 1.30-1.19 (m, 2H), 0.87 (t, J=7.4 Hz, 3H). $^{13}$C NMR (126 MHz, CDCl$_3$) δ 170.42, 167.72, 161.14, 138.75, 128.40, 127.99, 127.03, 70.82, 54.22, 50.38, 30.38, 29.77, 20.27, 14.06. MS (ESI-TOF) for C$_{16}$H$_{21}$IN$_4$ [M+H]$^+$ calculated 397.0884, found 397.0888.

4-Butoxy-5-iodo-6-methylpyrimidin-2-amine (4g)

To a solution of compound 3 (53.8 mg, 0.2 mmol) in 1-butanol (3 mL), was added K$_2$CO$_3$ (138 mg, 1 mmol). The reaction mixture was stirred for 24 h at 85° C. The reaction mixture was cooled to room temperature and the solvent was removed under reduced pressure. The reaction mixture was diluted with water and extracted with EtOAc (3×20 mL). The combined organic layer was dried over Na$_2$SO$_4$ and concentrated under reduced pressure, and the crude material was purified by flash chromatography (30% EtOAc/hexanes) to afford the compound 4g as a white solid (40 mg, 65%). $^1$H NMR (500 MHz, CDCl$_3$) δ 4.92 (s, 2H), 4.28 (t, J=6.6 Hz, 2H), 2.49 (s, 3H), 1.79-1.70 (m, 2H), 1.54-1.43 (m, 2H), 0.97 (t, J=7.4 Hz, 3H). $^{13}$C NMR (126 MHz, CDCl$_3$) δ 169.68, 168.10, 162.01, 67.60, 67.54, 30.88, 28.29, 19.35, 13.96. MS (ESI-TOF) for C$_9$H$_{14}$IN$_3$O [M+H]$^+$ calculated 308.0254, found 308.0250.

4-(Butylthio)-5-iodo-6-methylpyrimidin-2-amine (4h)

To a solution of compound 3 (53.8 mg, 0.2 mmol) in MeOH (3 mL), was added Et$_3$N (56 μL, 0.4 mmol) and 1-butanethiol (43 μL, 0.4 mmol). The reaction mixture was stirred for 12 h at 70° C. The reaction mixture was cooled to room temperature and the solvent was removed under reduced pressure. The reaction mixture was diluted with water and extracted with EtOAc (3×20 mL). The combined organic layer was dried over Na$_2$SO$_4$ and concentrated under reduced pressure, and the crude material was purified by flash chromatography (30% EtOAc/hexanes) to afford the compound 4h as a white solid (50 mg, 77%). $^1$H NMR (500 MHz, CDCl$_3$) δ 4.92 (s, 2H), 3.05 (t, J=7.4 Hz, 2H), 2.49 (s, 3H), 1.72-1.63 (m, 2H), 1.52-1.40 (m, 2H), 0.95 (t, J=7.4 Hz, 3H). $^{13}$C NMR (126 MHz, CDCl$_3$) δ 173.52, 167.19, 160.88, 81.55, 32.27, 30.95, 28.65, 22.26, 13.86. MS (ESI-TOF) for C$_9$H$_{14}$IN$_3$S [M+H]$^+$ calculated 324.0026, found 324.0021.

4-Methyl-6-(pent-1-yn-1-yl)pyrimidin-2-amine (4i)

To a solution of compound 2 (72 mg, 0.5 mmol) in 3:1 mixture of CH$_3$CN (6 mL) and Et$_3$N (3 mL) were added Pd(PPh$_3$)$_4$ (57.8 mg, 0.05 mmol) and CuI (19 mg, 0.1 mmol). The reaction mixture was degassed with dry nitrogen for 5 min., then 1-pentyne (98.5 μL, 1 mmol) was added. The resulting reaction mixture was stirred for 12 h under nitrogen atmosphere. After completion of the reaction, the reaction mixture was diluted with water and extracted with ethylacetate (3×30 mL). The combined organic layer was dried over Na$_2$SO$_4$, concentrated under reduced pressure, and the crude material was purified by flash chromatography (70% EtOAc/hexanes) to obtain the compound 4i as a pale yellow solid (65 mg, 74%). $^1$H NMR (500 MHz, CDCl$_3$) b 6.57 (s, 1H), 5.06 (s, 2H), 2.40 (t, J=7.1 Hz, 2H), 2.31 (s, 3H), 1.70-1.58 (m, 2H), 1.03 (t, J=7.4 Hz, 3H). $^{13}$C NMR (126 MHz, CDCl$_3$) δ 168.43, 162.92, 151.71, 113.30, 94.00, 79.32, 23.88, 21.77, 21.41, 13.70. MS (ESI-TOF) for C$_{10}$H$_{13}$N$_3$[M+H]$^+$ calculated 176.1182, found 176.1172.

4-Methyl-6-pentylpyrimidin-2-amine (4j)

To a solution of compound 4i (35.4 mg, 0.2 mmol) in anhydrous EtOAc (20 mL) was added a catalytic amount of Pd/C, and the reaction mixture was subjected to hydrogenation at 50 psi for 5 h. The reaction mixture was filtered, and the filtrate concentrated under reduced pressure. The crude material was purified using silica gel column chromatography (60% EtOAc/hexanes) to obtain 4j as white solid (30 mg, 84%). $^1$H NMR (500 MHz, CDCl$_3$) δ 6.36 (s, 1H), 5.11 (s, 2H), 2.49 (t, J=7.8 Hz, 2H), 2.29 (s, 3H), 1.69-1.59 (m, 2H), 1.37-1.28 (m, 4H), 0.88 (t, J=7.0 Hz, 3H). $^{13}$C NMR (126 MHz, CDCl$_3$) δ 172.04, 167.86, 162.97, 110.12, 37.84, 31.73, 28.68, 23.95, 22.62, 14.11. MS (ESI-TOF) for C$_{10}$H$_{17}$N$_3$[M+H]$^+$ calculated 180.1495, found 180.1486.

5-iodo-4-methyl-6-pentylpyrimidin-2-amine (4k)

To a solution of compound 4j (17.9 mg, 0.1 mmol) in anhydrous DMF (1 mL) was added NIS (22.5 mg, 1 mmol), and the reaction mixture was stirred for 12 h. The reaction mixture was diluted with water and extracted with EtOAc (3×10 mL). The combined organic layer was dried over Na$_2$SO$_4$, concentrated under reduced pressure, and the crude material was purified by flash chromatography (40% EtOAc/hexanes) to obtain the compound 4k as a white solid (25 mg, 82%). $^1$H NMR (500 MHz, CDCl$_3$) δ 5.02 (s, 2H), 2.77 (t, J=8.0 Hz, 2H), 2.54 (s, 3H), 1.68-1.61 (m, 2H), 1.42-1.32 (m, 4H), 0.91 (t, J=7.0 Hz, 3H). $^{13}$C NMR (126 MHz, CDCl$_3$) δ 172.78, 169.92, 162.02, 84.73, 41.50, 31.83, 29.70, 28.06, 22.61, 14.16. MS (ESI-TOF) for C$_{10}$H$_{16}$IN$_3$ [M+H]$^+$ calculated 306.0462, found 306.0459.

Compounds 5a and 5b were synthesized similarly as compound 3.

4,5-Dichloro-6-methylpyrimidin-2-amine (5a)

N-Chlorosuccinimide was used as reagent. White solid (126 mg, 71%). $^1$H NMR (500 MHz, DMSO-d$_6$) δ 7.17 (s, 2H), 2.36 (s, 3H). $^{13}$C NMR (126 MHz, DMSO-d$_6$) δ 166.74, 160.51, 156.68, 113.06, 22.68. MS (ESI-TOF) for C$_5$H$_5$Cl$_2$N$_3$[M+H]$^+$ calculated 177.9933, found 177.9962.

5-Bromo-4-chloro-6-methylpyrimidin-2-amine (5b)

N-Bromosuccinimide was used as reagent. White solid (155 mg, 70%). $^1$H NMR (500 MHz, DMSO-d$_6$) δ 7.18 (s, 2H), 2.40 (s, 3H). $^{13}$C NMR (126 MHz, DMSO-d$_6$) δ 168.47, 161.12, 158.71, 103.25, 25.21. MS (ESI-TOF) for C$_5$H$_5$BrClN$_3$ [M+H]$^+$ calculated 221.9428, found 221.9470.

Compounds 6a and 6b were synthesized similarly as compound 4b.

N$^4$-Butyl-5-chloro-6-methylpyrimidine-2,4-diamine (6a)

Compound 5a was used as reagent. White solid (34 mg, 79%). $^1$H NMR (500 MHz, CDCl$_3$) δ 5.17 (s, 1H), 4.78 (s, 2H), 3.43-3.35 (m, 2H), 2.28 (s, 3H), 1.62-1.52 (m, 2H), 1.44-1.33 (m, 2H), 0.94 (t, J=7.4 Hz, 3H). $^{13}$C NMR (126 MHz, CDCl$_3$) δ 160.68, 160.30, 158.43, 103.19, 40.83, 31.76, 21.69, 20.20, 13.95. MS (ESI-TOF) for C$_9$H$_{15}$ClN$_4$ [M+H]$^+$ calculated 215.1058, found 215.1050.

5-Bromo-N$^4$-butyl-6-methylpyrimidine-2,4-diamine (6b)

Compound 5b was used as reagent. White solid (45 mg, 87%). $^1$H NMR (500 MHz, CDCl$_3$) δ 5.24 (s, 1H), 4.80 (s, 2H), 3.41-3.36 (m, 2H), 2.32 (s, 3H), 1.62-1.52 (m, 2H), 1.44-1.33 (m, 2H), 0.94 (t, J=7.4 Hz, 3H). $^{13}$C NMR (126 MHz, CDCl$_3$) δ 162.57, 160.97, 159.11, 93.92, 41.10, 31.70, 24.23, 20.22, 13.96. MS (ESI-TOF) for C$_9$H$_5$BrN$_4$ [M+H]$^+$ calculated 259.0553, found 259.0543.

N$^4$-Butyl-5-fluoro-6-methylpyrimidine-2,4-diamine (6c)

To a solution of guanidine hydrochloride (95.5 mg, 1 mmol) in MeOH (5 mL), were added compound 7 (125 μL, 1 mmol) and Et$_3$N (280 μL, 2 mmol). The reaction mixture was refluxed for 12 h. The reaction mixture was cooled to room temperature, and the resulting precipitate was filtered and washed with methanol, to yield compound 8 as a white solid (100 mg, 69%). A suspension of compound 8 (71.5 mg, 0.5 mmol) in phosphorus(V) oxychloride was placed in a pressure vessel. The reaction mixture was stirred for 3 h at 85° C. The reaction mixture was cooled to room temperature and the solvent was removed under reduced pressure. The reaction mixture was diluted with water and extracted with EtOAc (3×20 mL). The combined organic layer was dried over Na$_2$SO$_4$ and concentrated under reduced pressure, and the crude material was purified by flash chromatography (40% EtOAc/hexanes) to afford the compound 9 as a white solid (50 mg, 62%). MS (ESI-TOF) for C$_5$H$_5$ClFN$_3$ [M+H]$^+$ calculated 162.0229, found 162.0278. To a solution of 9 (32.3 mg, 0.2 mmol) in MeOH (3 mL), was added Et$_3$N (56 μL, 0.4 mmol) and butylamine (39.5 μL, 0.4 mmol). The reaction mixture was stirred for 12 h at 70° C. The reaction mixture was cooled to room temperature and the solvent was removed under reduced pressure. The reaction mixture was diluted with water and extracted with EtOAc (3×20 mL). The combined organic layer was dried over Na$_2$SO$_4$ and concentrated under reduced pressure, and the crude material was purified by flash chromatography (80% EtOAc/hexanes) to afford the compound 6c as a white solid (30 mg, 76%). $^1$H NMR (500 MHz, CDCl$_3$) δ 4.76 (s, 1H), 4.58 (s, 2H), 3.44-3.36 (m, 2H), 2.18 (d, J=2.9 Hz, 3H), 1.62-1.52 (m, 2H), 1.45-1.34 (m, 2H), 0.95 (t, J=7.4 Hz, 3H). $^{13}$C NMR (126 MHz, CDCl$_3$) δ 158.14 (d, J=5.1 Hz), 152.99 (d, J=12.7 Hz), 147.58 (d, J=13.7 Hz), 139.53 (d, J=238.8 Hz). 40.31, 31.88, 20.18, 16.61, 13.95. MS (ESI-TOF) for C$_9$H$_{15}$FN$_4$ [M+H]$^+$ calculated 199.1354, found 199.1347.

Compound 11 was synthesized similarly as compound 3.

4-Chloro-5-iodopyrimidin-2-amine (11)

4-Chloropyrimidin-2-amine (10) was used as reagent. White solid (170 mg, 67.5%). MS (ESI-TOF) for C$_4$H$_3$ClIN$_3$ [M+H]$^+$ calculated 255.9133, found 255.9205.

Compounds 15-20 were synthesized similarly as compound 4b.

N$^4$-Butyl-6-methylpyrimidine-2,4-diamine (15)

4-Chloro-6-methylpyrimidin-2-amine (2) was used as reagent. White solid (28 mg, 78%). $^1$H NMR (500 MHz, CDCl$_3$) δ 5.61 (s, 1H), 4.81 (s, 2H), 4.72 (s, 1H), 3.24-3.16 (m, 2H), 2.18 (s, 3H), 1.58-1.49 (m, 2H), 1.43-1.31 (m, 2H), 0.92 (t, J=7.3 Hz, 3H). $^{13}$C NMR (126 MHz, CDCl$_3$) δ 166.28, 164.06, 162.81, 93.09, 41.16, 31.67, 23.97, 20.18, 13.89. MS (ESI-TOF) for C$_9$H$_{14}$N$_4$ [M+H]$^+$ calculated 181.1448, found 181.1442.

N$^4$-Butylpyrimidine-2,4-diamine (16)

4-Chloropyrimidin-2-amine (10) was used as reagent. White solid (25 mg, 75%). $^1$H NMR (500 MHz, CDCl$_3$) δ 7.81 (d, J=5.9 Hz, 1H), 5.74 (d, J=5.9 Hz, 1H), 4.84 (s, 3H), 3.26-3.18 (m, 2H), 1.60-1.50 (m, 2H), 1.44-1.32 (m, 2H), 0.93 (t, J=7.3 Hz, 3H). $^{13}$C NMR (126 MHz, CDCl$_3$) δ

163.55, 162.96, 156.60, 94.73, 41.13, 31.62, 20.18, 13.89. MS (ESI-TOF) for $C_8H_{14}N_4$[M+H]$^+$ calculated 167.1291, found 167.1282.

N$^4$-Butyl-5-iodopyrimidine-2,4-diamine (17)

4-Chloro-5-iodopyrimidin-2-amine (11) was used as reagent. White solid (42 mg, 72%). $^1$H NMR (500 MHz, CDCl$_3$) δ 7.99 (s, 1H), 5.07 (s, 1H), 4.78 (s, 2H), 3.44-3.36 (m, 2H), 1.63-1.53 (m, 2H), 1.46-1.34 (m, 2H), 0.96 (t, J=7.4 Hz, 3H). $^{13}$C NMR (126 MHz, CDCl$_3$) δ 162.41, 161.60, 160.26, 65.42, 41.21, 31.56, 20.24, 13.98. MS (ESI-TOF) for $C_8H_{13}IN_4$ [M+H]$^+$ calculated 293.0258, found 293.0251.

N$^4$-Butylpyrimidine-2,4,6-triamine (18)

6-Chloropyrimidine-2,4-diamine (12) was used as reagent. Pale yellow solid (25 mg, 69%). $^1$H NMR (500 MHz, CDCl$_3$) δ 4.95 (s, 1H), 4.57 (s, 3H), 4.44 (s, 2H), 3.15-3.08 (m, 2H), 1.59-1.49 (m, 2H), 1.44-1.32 (m, 2H), 0.93 (t, J=7.4 Hz, 3H). $^{13}$C NMR (126 MHz, CDCl$_3$) δ 164.50, 164.45, 162.68, 74.37, 41.53, 31.56, 20.24, 13.91. MS (ESI-TOF) for $C_8H_{15}N_5$[M+H]$^+$ calculated 182.1400, found 182.1389.

N$^4$-Butyl-6-methoxypyrimidine-2,4-diamine (19)

4-Chloro-6-methoxypyrimidin-2-amine (13) was used as reagent. White solid (32 mg, 82%). $^1$H NMR (500 MHz, CDCl$_3$) δ 5.12 (s, 1H), 4.74 (s, 2H), 4.69 (s, 1H), 3.81 (s, 3H), 3.18-3.10 (m, 2H), 1.59-1.49 (m, 2H), 1.43-1.31 (m, 2H), 0.92 (t, J=7.3 Hz, 3H). $^{13}$C NMR (126 MHz, CDCl$_3$) δ 171.75, 165.40, 162.52, 75.70, 53.39, 41.55, 31.51, 20.20, 13.88. MS (ESI-TOF) for $C_9H_{16}N_4O$ [M+H]$^+$ calculated 197.1397, found 197.1392.

N$^4$-Butyl-6-chloropyrimidine-2,4-diamine (20)

4,6-Dichloropyrimidin-2-amine (14) was used as reagent. White solid (34 mg, 84%). $^1$H NMR (500 MHz, CDCl$_3$) δ 5.74 (s, 1H), 5.35 (s, 3H), 3.26-3.06 (m, 2H), 1.57-1.47 (m, 2H), 1.40-1.29 (m, 2H), 0.90 (t, J=7.4 Hz, 3H). $^{13}$C NMR (126 MHz, CDCl$_3$) δ 164.40, 162.57, 159.89, 91.77, 41.30, 31.43, 20.09, 13.81. MS (ESI-TOF) for $C_8H_{13}ClN_4$ [M+H]$^+$ calculated 201.0902, found 201.0895.

Compounds 21-23 were synthesized similarly as compound 4k.

N$^4$-Butyl-5-iodopyrimidine-2,4,6-triamine (21)

Compound 18 was used as reagent. Pale yellow solid (15 mg, 49%). $^1$H NMR (500 MHz, CDCl$_3$) δ 4.92 (s, 1H), 4.81 (s, 2H), 4.60 (s, 2H), 3.44-3.35 (m, 2H), 1.62-1.52 (m, 2H), 1.45-1.34 (m, 2H), 0.95 (t, J=7.4 Hz, 3H). $^{13}$C NMR (126 MHz, CDCl$_3$) δ 162.12, 161.66, 161.49, 46.15, 41.67, 32.00, 20.25, 14.02. MS (ESI-TOF) for $C_8H_{14}IN_5$ [M+H]$^+$ calculated 308.0367, found 308.0336.

N$^4$-Butyl-5-iodo-6-methoxypyrimidine-2,4-diamine (22)

Compound 19 was used as reagent. White solid (22 mg, 68%). $^1$H NMR (500 MHz, CDCl$_3$) δ 5.06 (s, 1H), 4.71 (s, 2H), 3.87 (s, 3H), 3.43-3.35 (m, 2H), 1.62-1.52 (m, 2H), 1.45-1.33 (m, 2H), 0.95 (t, J=7.4 Hz, 3H). $^{13}$C NMR (126 MHz, CDCl$_3$) δ 167.90, 162.50, 162.34, 54.44, 46.69, 41.67, 31.94, 20.23, 14.00. MS (ESI-TOF) for $C_9H_{15}IN_4O$ [M+H]$^+$ calculated 323.0363, found 323.0362.

N$^4$-Butyl-6-chloro-5-iodopyrimidine-2,4-diamine (23)

Compound 20 was used as reagent. White solid (23 mg, 70%). $^1$H NMR (500 MHz, DMSO-d$_6$) δ 6.54 (s, 2H), 6.45 (t, J=5.8 Hz, 1H), 3.35-3.27 (m, 2H), 1.54-1.44 (m, 2H), 1.33-1.22 (m, 2H), 0.89 (t, J=7.4 Hz, 3H). $^{13}$C NMR (126 MHz, DMSO-d$_6$) δ 162.48, 161.89, 161.12, 61.91, 40.94, 30.92, 19.56, 13.78. MS (ESI-TOF) for $C_8H_{12}ClIN_4$ [M+H]$^+$ calculated 326.9868, found 326.9863.

5-Benzyl-MN-butyl-6-methylpyrimidine-2,4-diamine (24)

To a solution of compound 4b (30.6 mg, 0.1 mmol), benzylboronic acid pinacol ester (44.4 μL, 0.2 mmol) and K$_2$CO$_3$ (55 mg, 0.4 mmol) in 4:1 mixture of 1,4-dioxane (2 mL) and water (0.5 mL) was added Pd(dppf)Cl$_2$ (7.3 mg, 0.01 mmol). The reaction mixture was degassed with dry nitrogen for 5 min, then stirred for 12 h at 85° C. under nitrogen atmosphere. The reaction mixture was diluted with water and extracted with EtOAc (3×20 mL). The combined organic layer was dried over Na$_2$SO$_4$, concentrated under reduced pressure, and the crude material was purified by flash chromatography (10% MeOH/CH$_2$Cl$_2$) to obtain the compound 24 as a pale yellow solid (20 mg, 74%). $^1$H NMR (500 MHz, MeOD) δ 7.29-7.24 (m, 2H), 7.20-7.16 (m, 1H), 7.15-7.10 (m, 2H), 3.81 (s, 2H), 3.34-3.29 (m, 2H), 2.16 (s, 3H), 1.49-1.39 (m, 2H), 1.24-1.12 (m, 2H), 0.85 (t, J=7.4 Hz, 3H). $^{13}$C NMR (126 MHz, MeOD) δ 163.45, 162.37, 162.24, 140.45, 129.59, 128.74, 127.29, 105.17, 41.44, 32.55, 31.31, 20.93, 20.88, 14.15. MS (ESI-TOF) for $C_{16}H_{22}N_4$ [M+H]$^+$ calculated 271.1917, found 271.1917.

5-(3-Aminopropyl)-N$^4$-butyl-6-methylpyrimidine-2, 4-diamine dihydrochloride (27a)

To a solution of compound 4b (92 mg, 0.3 mmol) in 3:1 mixture of DMF (6 mL) and DIPEA (3 mL) were added Pd(PPh$_3$)$_4$ (34.6 mg, 0.03 mmol) and CuI (11.4 mg, 0.06 mmol). The reaction mixture was degassed with dry nitrogen for 5 min, then N-boc-propargylamine (93 mg, 0.6 mmol) was added. The resulting reaction mixture was stirred for 12 h under nitrogen atmosphere. After completion of the reaction, the mixture was diluted with water and extracted with ethylacetate (3×30 mL). The combined organic layer was dried over Na$_2$SO$_4$ and concentrated under reduced pressure, the crude material was purified by flash chromatography (90% EtOAc/hexanes) to obtain the compound 25a as yellow oil (72 mg, 72%). MS (ESI-TOF) for $C_{17}H_{27}N_5O_2$ [M+H]$^+$ calculated 334.2238, found 334.2254. To a solution of compound 25a (33.3 mg, 0.1 mmol) in anhydrous EtOAc (10 mL) was added a catalytic amount of Pd/C, and the reaction mixture was subjected to hydrogenation at 50 psi for 5 h. The reaction mixture was filtered, and the filtrate concentrated under reduced pressure. The crude material was purified by flash chromatography (20% MeOH/CH$_2$Cl$_2$) to obtain N-boc protected alkylamine 26a as a pale oil (24 mg, 71%). MS (ESI-TOF) for $C_{17}H_{31}N_5O_2$ [M+H]$^+$ calculated 338.2551, found 338.2698. To a stirred solution of N-boc protected alkylamine 26a (17 mg, 0.05 mmol) in 1,4-dioxane (1 mL) was added hydrogen chloride (1 mL, 4 M in dioxane), and the reaction mixture was stirred for 3 h at room temperature. Excess solvent was removed under reduced pressure and the resulted residue was thoroughly washed with diethyl ether to obtain the desired compound 27a as a white solid (12 mg, 77%). $^1$H NMR (500 MHz, MeOD) δ 3.53 (t, J=7.3 Hz, 2H), 3.05 (t, J=7.6 Hz, 2H), 2.56 (t, J=8.0 Hz, 2H), 2.32 (s, 3H), 1.84-1.73 (m, 2H), 1.68-1.58 (m, 2H), 1.43-1.32 (m, 2H), 0.96 (t, J=7.4 Hz, 3H). $^{13}$C NMR (126 MHz, MeOD) δ 163.44, 155.71, 149.22, 107.20, 42.26, 40.08, 32.19, 27.02, 22.19, 21.14, 16.50, 14.17. MS (ESI-TOF) for $C_{12}H_2N_5$ [M+H]$^+$ calculated 238.2026, found 238.2021.

Compounds 27b and 27c were synthesized similarly as compound 27a.

5-(4-Aminobutyl)-N-butyl-6-methylpyrimidine-2,4-diamine dihydrochloride (27b)

Intermediate compound 25b. Yellow oil (75 mg, 72%). MS (ESI-TOF) for $C_{18}H_{29}N_5O_2$ [M+H]$^+$ calculated 348.2394, found 348.2407.

Intermediate compound 26b. Pale oil (25 mg, 71%). MS (ESI-TOF) for $C_{18}H_{33}N_5O_2$[M+H]$^+$ calculated 352.2707, found 352.2755).

Compound 27b: White solid (13 mg, 80%). $^1$H NMR (500 MHz, MeOD) δ 3.52 (t, J=7.3 Hz, 2H), 2.96 (t, J=7.7 Hz, 2H), 2.51 (t, J=8.0 Hz, 2H), 2.30 (s, 3H), 1.81-1.71 (m, 2H), 1.67-1.59 (m, 2H), 1.55-1.46 (m, 2H), 1.43-1.32 (m, 2H), 0.96 (t, J=7.4 Hz, 3H). $^{13}$C NMR (126 MHz, MeOD) δ 163.60, 155.67, 148.81, 108.22, 42.26, 40.60, 32.21, 28.20, 26.17, 24.58, 21.16, 16.56, 14.19. MS (ESI-TOF) for $C_{13}H_{25}N_5$ [M+H]$^+$ calculated 252.2183, found 252.2182.

5-(5-Aminopentyl)-MN-butyl-6-methylpyrimidine-2,4-diamine dihydrochloride (27c)

Intermediate compound 25c. Yellow oil (75 mg, 69%). MS (ESI-TOF) for $C_{19}H_{31}N_5O_2$ [M+H]$^+$ calculated 362.2551, found 362.2578.

Intermediate compound 26c. Pale oil (28 mg, 77%). MS (ESI-TOF) for $C_{19}H_{35}N_5O_2$[M+H]$^+$ calculated 366.2864, found 366.2897.

Compound 27c. White solid (13 mg, 77%). $^1$H NMR (500 MHz, MeOD) δ 3.52 (t, J=7.3 Hz, 2H), 2.94 (t, J=7.6 Hz, 2H), 2.49 (t, J=7.0 Hz, 2H), 2.30 (s, 3H), 1.74-1.69 (m, 2H), 1.64-1.57 (m, 2H), 1.54-1.46 (m, 4H), 1.43-1.31 (m, 2H), 0.96 (t, J=7.4 Hz, 3H). $^{13}$C NMR (126 MHz, MeOD) δ 163.62, 155.63, 148.53, 108.60, 42.18, 40.59, 32.21, 28.76, 28.51, 27.05, 24.85, 21.14, 16.57, 14.19. MS (ESI-TOF) for $C_{14}H_{27}N_5$ [M+H]$^+$ calculated 266.2339, found 266.2335.

N$^4$-Butyl-6-phenylpyrimidine-2,4-diamine (28)

To a solution of compound 20 (400 mg, 2 mmol), phenylboronic acid (366 mg, 3 mmol) and $K_2CO_3$ (828 mg, 6 mmol) in 4:1 mixture of 1,4-dioxane (8 mL) and water (2 mL) was added Pd(dppf)Cl$_2$ (73.1 mg, 0.1 mmol). The reaction mixture was degassed with dry nitrogen for 5 min, then stirred for 12 h at 85° C. under nitrogen atmosphere. The reaction mixture was diluted with water and extracted with EtOAc (3×50 mL). The combined organic layer was dried over Na$_2$SO$_4$ and concentrated under reduced pressure, and the crude material was purified by flash chromatography (80% EtOAc/hexanes) to obtain the compound 28 as a white solid (420 mg, 87%). $^1$H NMR (500 MHz, CDCl$_3$) δ 7.93-7.87 (m, 2H), 7.47-7.38 (m, 3H), 6.16 (s, 1H), 4.78 (s, 2H), 4.73 (s, 1H), 3.36-3.28 (m, 2H), 1.65-1.56 (m, 2H), 1.49-1.37 (m, 2H), 0.96 (t, J=7.4 Hz, 3H). $^{13}$C NMR (126 MHz, CDCl$_3$) δ 164.70, 164.47, 163.28, 138.70, 129.76, 128.62, 126.96, 90.86, 41.30, 31.70, 20.22, 13.93. MS (ESI-TOF) for $C_{14}H_{18}N_4$ [M+H]$^+$ calculated 243.1604, found 243.1596.

Compound 29 was synthesized similarly as compound 3.

N$^4$-Butyl-5-iodo-6-phenylpyrimidine-2,4-diamine (29)

Compound 28 was used as reagent. White solid (300 mg, 82%). $^1$H NMR (500 MHz, CDCl$_3$) δ 7.46-7.45 (m, 2H), 7.43-7.37 (m, 3H), 5.48 (t, J=5.5 Hz, 1H), 4.92 (s, 2H), 3.49-3.41 (m, 2H), 1.67-1.57 (m, 2H), 1.49-1.38 (m, 2H), 0.98 (t, J=7.3 Hz, 3H). $^{13}$C NMR (126 MHz, CDCl$_3$) 5167.91, 162.20, 161.53, 142.01, 128.86, 128.55, 128.15, 67.28, 41.74, 31.58, 20.29, 14.01. MS (ESI-TOF) for $C_{14}H_{17}IN_4$ [M+H]$^+$ calculated 369.0571, found 369.0572.

Compounds 32a-c were synthesized similarly as compound 27a.

5-(3-Aminopropyl)-M-butyl-6-phenylpyrimidine-2,4-diamine dihydrochloride (32a)

Intermediate compound 30a. Yellow oil (90 mg, 76%). MS (ESI-TOF) for $C_{22}H_{29}N_5O_2$ [M+H]$^+$ calculated 396.2394, found 396.2447.

Intermediate compound 31a. Pale oil (32 mg, 80%, MS (ESI-TOF) for $C_{22}H_{33}N_5O_2$[M+H]$^+$ calculated 400.2707, found 400.2723).

Compound 32a. White solid (15 mg, 81%). $^1$H NMR (500 MHz, MeOD) δ 7.64-7.58 (m, 3H), 7.56-7.49 (m, 2H), 3.62 (t, J=7.3 Hz, 2H), 2.81 (t, J=7.9 Hz, 2H), 2.49 (t, J=8.1 Hz, 2H), 1.83-1.74 (m, 2H), 1.73-1.65 (m, 2H), 1.47-1.38 (m, 2H), 0.99 (t, J=7.4 Hz, 3H). $^{13}$C NMR (126 MHz, MeOD) δ 163.69, 155.80, 150.93, 133.01, 131.88, 130.47, 129.63, 107.90, 42.48, 40.04, 32.16, 27.43, 22.94, 21.23, 14.23. MS (ESI-TOF) for $C_{17}H_{25}N_5$ [M+H]$^+$ calculated 300.2183, found 300.2177.

5-(4-Aminobutyl)-N$^4$-butyl-6-phenylpyrimidine-2,4-diamine dihydrochloride (32b)

Intermediate compound 30b. Yellow oil (75 mg, 61%). MS (ESI-TOF) for $C_{23}H_{31}N_5O_2$ [M+H]$^+$ calculated 410.2551, found 410.1983.

Intermediate compound 31b. Pale oil (28 mg, 68%). MS (ESI-TOF) for $C_{23}H_{35}N_5O_2$ [M+H]$^+$ calculated 414.2864, found 414.2263.

Compound 32b. White solid (16 mg, 83%). $^1$H NMR (500 MHz, MeOD) δ 7.63-7.57 (m, 3H), 7.55-7.48 (m, 2H), 3.60 (t, J=7.3 Hz, 2H), 2.76 (t, J=7.1 Hz, 2H), 2.44 (t, J=7.3 Hz, 2H), 1.73-1.63 (m, 2H), 1.55-1.48 (m, 4H), 1.46-1.38 (m, 2H), 0.99 (t, J=7.4 Hz, 3H). $^{13}$C NMR (126 MHz, MeOD) δ 163.86, 155.75, 150.59, 133.28, 131.80, 130.37, 129.69, 108.87, 42.45, 40.31, 32.16, 28.05, 26.47, 25.13, 21.22, 14.21. MS (ESI-TOF) for $C_{18}H_{27}N_5$[M+H]$^+$ calculated 314.2339, found 314.2335.

5-(5-Aminopentyl)-N$^4$-butyl-6-phenylpyrimidine-2,4-diamine dihydrochloride (32c)

Intermediate compound 30c. Yellow oil (80 mg, 63%). MS (ESI-TOF) for $C_{24}H_{33}N_5O_2$ [M+H]$^+$ calculated 424.2707, found 424.2770.

Intermediate compound 31c. Pale oil (30 mg, 70%). MS (ESI-TOF) for $C_{24}H_{37}N_5O_2$ [M+H]$^+$ calculated 428.3020, found 428.3051.

Compound 32c. White solid (16 mg, 80%). $^1$H NMR (500 MHz, MeOD) δ 7.61-7.57 (m, 3H), 7.53-7.49 (m, 2H), 3.60 (t, J=7.3 Hz, 2H), 2.81 (t, J=7.7 Hz, 2H), 2.41 (t, J=8.0 Hz, 2H), 1.73-1.63 (m, 2H), 1.57-1.36 (m, 6H), 1.34-1.23 (m, 2H), 0.99 (t, J=7.4 Hz, 3H). $^{13}$C NMR (126 MHz, MeOD) δ 163.89, 155.70, 150.27, 133.34, 131.71, 130.30, 129.67, 109.34, 42.36, 40.45, 32.15, 29.03, 28.13, 26.91, 25.34, 21.20, 14.21. MS (ESI-TOF) for $C_{19}H_{29}N_5$ [M+H]$^+$ calculated 328.2496, found 328.2493.

Human TLR8-Specific Reporter Gene Assays (NF-κB Induction), and TLR-2/-3/-4/-5/-7/-9 Counter-Screens:

The induction of NF-κB was quantified using human TLR-2/-3/-4/-5/-7/-8/-9-specific, rapid-throughput, liquid handler-assisted reporter gene assays as previously described by us.[31,25, 32,33] HEK293 cells stably co-transfected with the appropriate hTLR and secreted alkaline phosphatase (sAP) were maintained in HEK-Blue™ Selection medium. Stable expression of secreted alkaline phosphatase (sAP) under control of NF-κB/AP-1 promoters is inducible by appropriate TLR agonists, and extracellular sAP in the supernatant is proportional to NF-κB induction. Reporter cells were incubated at a density of ~10$^5$ cells/ml in a volume of 80 μl/well, in 384-well, flat-bottomed, cell culture-treated microtiter plates in the presence of graded concentrations of stimuli. sAP was assayed spectrophotometrically using an alkaline phosphatase-specific chromogen (present in HEK-detection medium as supplied by InvivoGen) at 620 nm.

Immunoassays for Cytokines.

Fresh human peripheral blood mononuclear cells (hPBMC) were isolated from human blood obtained by venipuncture in Cell Preparation Tubes (CPT, Beckton-Dickinson) with informed consent and as per guidelines approved by the University of Minnesota Human Subjects Experimentation Committee. Aliquots of PBMCs (10$^5$ cells in 100 □L/well) were stimulated for 16 h with graded concentrations of test compounds. Supernatants were isolated by centrifugation, and were assayed in duplicates using analyte-specific multiplexed cytokine/chemokine bead array assays (HCYTMAG-60K-PX29 MILLIPLEX MAP Human Cytokine/Chemokine Magnetic Bead Panel, EMD Millipore, Billerica, Mass.) as reported by us previously.[19] The following analytes were quantified: sCD40L, VEGF, TNF-β, TNF-α. TGF-α, RANTES, PDGF-AB/BB, PDGF-AA, MIP-1β, MIP-1α, MDC (CCL22), MCP-3, MCP-1, IP-10, IL-17A, IL-15, IL-13, IL-12 (p70), IL-12 (p40). IL-10, IL-9, IL-8, IL-7, IL-6, IL-5, IL-4, IL-3, IL-2, IL-1 ra, IL-1β, IL-1α, IFN-γ, IFN-α2, GRO, GM-CSF, G-CSF, fractalkine, Flt-3 ligand, FGF-2, eotaxin, EGF.

Flow-Cytometric Immunostimulation Experiments:

Cell surface marker upregulation was determined by flow cytometry using protocols published by us previously. Briefly, heparin-anticoagulated whole blood samples were obtained by venipuncture from healthy human volunteers with informed consent and as per guidelines approved by the University of Minnesota Human Subjects Experimentation Committee. Serial dilutions of selected compounds were performed using a Bio-Tek Precision 2000 XS liquid handler in sterile 96-well polypropylene plates, to which were added 100 μL aliquots of anticoagulated whole human blood. The plates were incubated at 37° C. for 16 h. Negative (DMSO) controls were included in each experiment. The following fluorochrome-conjugated antibodies were used: CD14-FITC, CD40-APC, CD80-PE-Cy7, CD86-V450 (Becton-Dickinson Biosciences, San Jose, Calif.). Following incubation, 2.5 μg of each antibody was added to wells with a liquid handler, and incubated at 4° C. in the dark for 60 min. Following staining, erythrocytes were lysed and leukocytes fixed by mixing 200 μL of the samples in 800 μL pre-warmed Whole Blood Lyse/Fix Buffer (Becton-Dickinson Biosciences, San Jose, Calif.) in 96 deep-well plates. After washing the cells twice at 300 g for 10 minutes in RPMI, the cells were transferred to a 96-well plate. Flow cytometry was performed using a BD FACSVerse instrument for acquisition on 200,000 gated events. Compensation for spillover was computed for each experiment on singly-stained Ultra-Comp Beads (eBioscience, Inc., San Diego, Calif.).

The discovery and development of safe and effective vaccine adjuvants has led to the exploration of structure-activity relationships (SAR) in a variety of innate immune-stimulatory chemotypes. A multiplexed, reporter gene-based high-throughput screen with a view to identifying novel immunostimulatory molecular classes was conducted. The screen yielded 552 provisional hits that were identified from among 123,943 compounds. Deconvolution and validation of hits led to the identification of N$^4$-butyl-5-iodo-6-methylpyrimidine-2,4-diamine (4b, Scheme 1) as a pure TLR8 agonist.

SAR studies on 4b began with the re-synthesis of the hit, as well as a verification of optimal alkyl chain length which had been previously shown to be a one important determinant of activity. Compound 4b (N$^4$-butyl), its homologs 4c (N$^4$-pentyl), 4d (M-hexyl), as well as a shorter-chain analogue 4a (N$^4$-propyl) were synthesized in a straightforward manner from commercially-available 4-chloro-6-methylpyrimidin-2-amine by iodination at C5 and aromatic nucleophilic substitution with alkylamines (Scheme 1). Primary screens in reporter gene assays verified that 4b was a bona fide TLR8-specific agonist, and the N$^4$-butyl substituent in 4b was optimal (EC$_{50}$: 1.64 μM, FIG. 2). The C4-amine appeared to serve as a H-bond donor, since substitutions of the amine (4e, 4f) abrogated activity. This was borne out in the bioisosteric 4-butoxy (4g) and 4-thiobutyl (4h) analogues which were also inactive. However, it had previously been observed in the case of the 3-alkyl-quinoline-2-amines that the C-alkyl compound, exemplified by 1c (FIG. 1), was significantly more active than its heteroatom-linked congeners, it was sought to synthesize the C-alkyl analogue with a chain length comparable to that of 4b. The pentyl-substituted pyrimidine analogue 4k was accessed via Sonogashira coupling of 2 with 1-pentyne, reduction of the alkyne, followed by iodination (Scheme 1). Compound 4k as well as its precursors 4j and 4i were found to be inactive, indicating that a H-bond donor functionality was indispensable at C4.

The influence of various halogens at C5 was systematically examined. The 5-chloro and 5-bromo analogues (6a and 6b, respectively) were obtained from 2 using conventional method (Scheme 1). It was found it expedient to synthesize the 5-fluoro substituted 6c by standard condensation-cyclization of 2-fluoroethylacetoacetate with guanidine via the 4-hydroxy-2-amino-5-fluoro-6-methylpyrimidine intermediate (Scheme 1). Replacement of the 5-iodo group with chloro (6a), bromo (6b), or fluoro (6c) groups led to substantial losses in potency.

Figure 2:
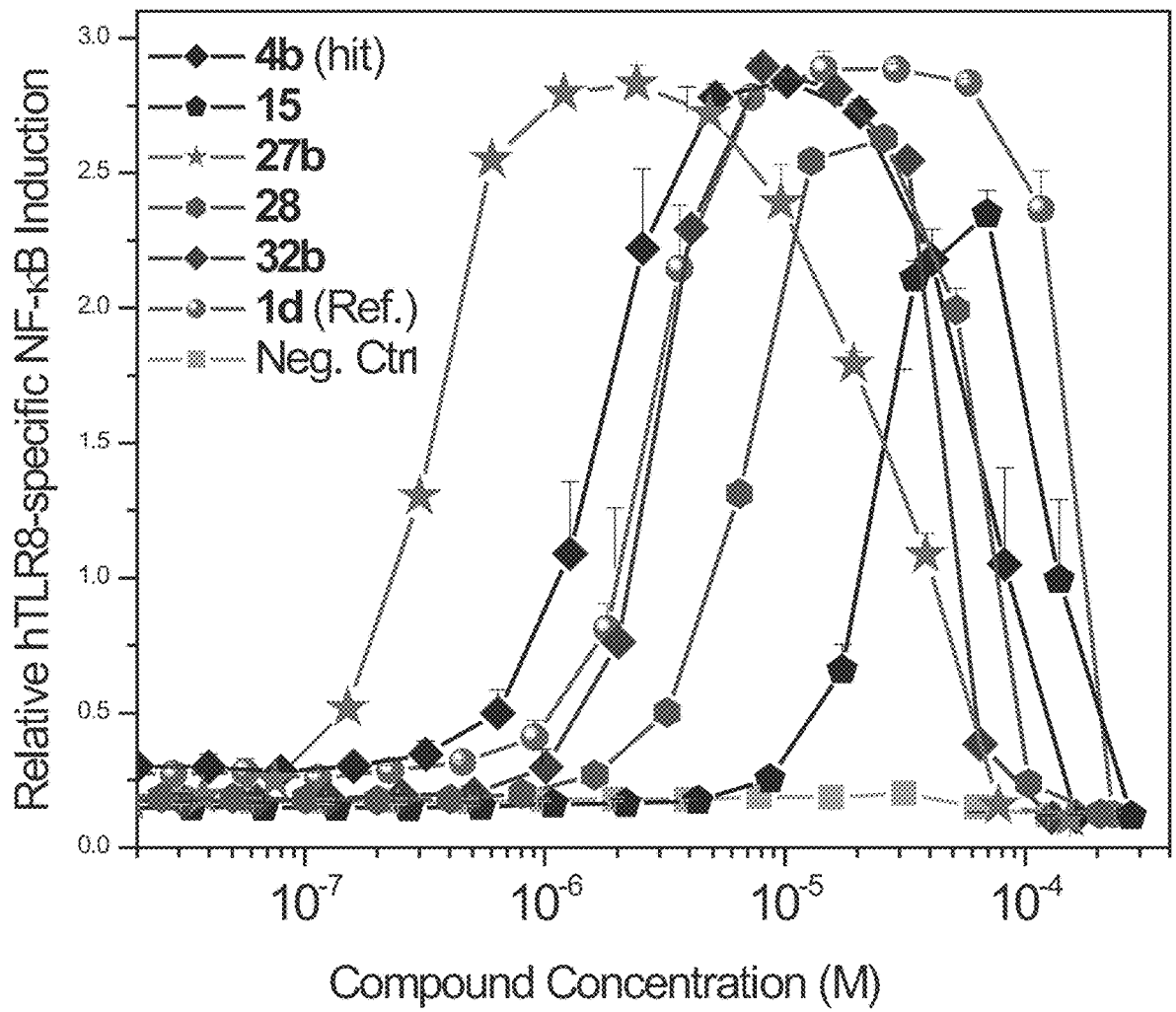
FIG. 2 is a plot of relative hTL8-specific NF-κB induction as a function of compound concentration.

The consequences of replacing the 6-methyl group of 4b were explored, holding the N$^4$-butyl group invariant. These target compounds (15-23) were readily accessed from commercially-available substituted 2-amino-4-chloropyrimidines (Scheme 2). The EC$_{50}$ of the des-iodo analogue 15 was 22 μM (ca. fourteen-fold less active than 4b; FIG. 2); the des-iodo, des-methyl compound 16 was not as active (EC$_{50}$: 73.2 μM); and the des-methyl analogue 17 was entirely without measurable TLR8-agonistic activity. The retention of activity in 15 prompted the exploration of analogues with various electron-donating and -withdrawing groups at C6, in the presence or absence of iodo substitution at C5 (18-23);

all of these compounds, however, were inactive, pointing strongly to electronic, rather than steric effects of substitutions at C6.

Mindful of the prominent π,π-interactions that had previously been observed in the crystal structures of a variety of chemotypes with Phe405 in TLR8, it was asked if functionalizing C5 with a bulky aromatic group would enhance potency. The C5-benzyl analogue 24, synthesized from 4b via conventional Suzuki coupling (Scheme 3), resulted in diminution of activity, exhibiting greatly attenuated area-under-the curve in dose-response assays. In the course of exploring several chemotypes, it had been observed that such compounds are inactive in secondary screens.

In previous efforts, crystallographic observations in two regioisomeric, dual TLR7/8-active imidazoquinolines had suggested that the formation of a strong ionic H-bond (salt bridge) with the side chain carboxylate of Asp545 not only resulted in enhancement of agonistic activity in primary screens, but also in higher proinflammatory cytokine induction in whole human blood assays; this hypothesis was successfully tested, whereby strategically grafting an aminoalkyl group on an aminoquinoline scaffold resulted in a twenty-fold enhancement of potency. Attention was therefore turned to 5-alkylamino derivatives of 15. Sonogashira coupling of 4b with amino-substituted alkynes (Scheme 3) afforded access to compounds 27a-c (propyl-, butyl-, pentyl-amino derivatives). The potency of the propylamino derivative 27a increased nearly ten-fold (2.31 µM) relative to that of 4b (22 µM); the potency of the butylamino compound 27b was ca. 74-fold higher (0.3 µM; FIG. 2) and appeared to plateau with the pentylamine homologue, 27c. This approach not only resulted in enhanced potency, but also obviated potential thyrotoxicity associated with iodinated aromatic compounds.

In earlier work on the exploration of SAR in the 2-aminoimidazoles, it had observed that the introduction of a phenyl group at C4 allowed for aromatic stacking with near-perfect coplanarity between the C4-phenyl ring of Phe405 of TLR8; the C4-phenyl group was accommodated in a pocket tightly circumscribed and delimited by the hydrophobic residues Tyr353, Val378, Val520 and Gln519. Enhancement of the potency in the C5-derivatized analogue 24 was not successful, and it remained to explore the functionalization of C6. The C6-phenyl analogue 28, synthesized via Suzuki coupling (Scheme 4) resulted in a TLR8-selective agonist with an $EC_{50}$ of 6.7 µM (FIG. 2). It was surprisingly and unexpectedly found that its 5-iodo derivative 29 was inactive. Compound 29 served as a convenient substrate for the syntheses of the 5-alkylamino derivatives 32a-c (Scheme 4). Activity in TLR8-specific primary screen was reinstated in the 5-butylamino (32b; $EC_{50}$: 2.7 µM) and 5-pentylamino (32c; $EC_{50}$: 2.35 µM) analogues, similar to what had been observed in the 27a-c series of compounds. The presence of the alkylamino group at C5 in both the 27b-c and 32b-c series of compounds not only served to enhance potency, but perhaps also obviates potential Phase 1 metabolism at this electron-rich site.

Figure 3:
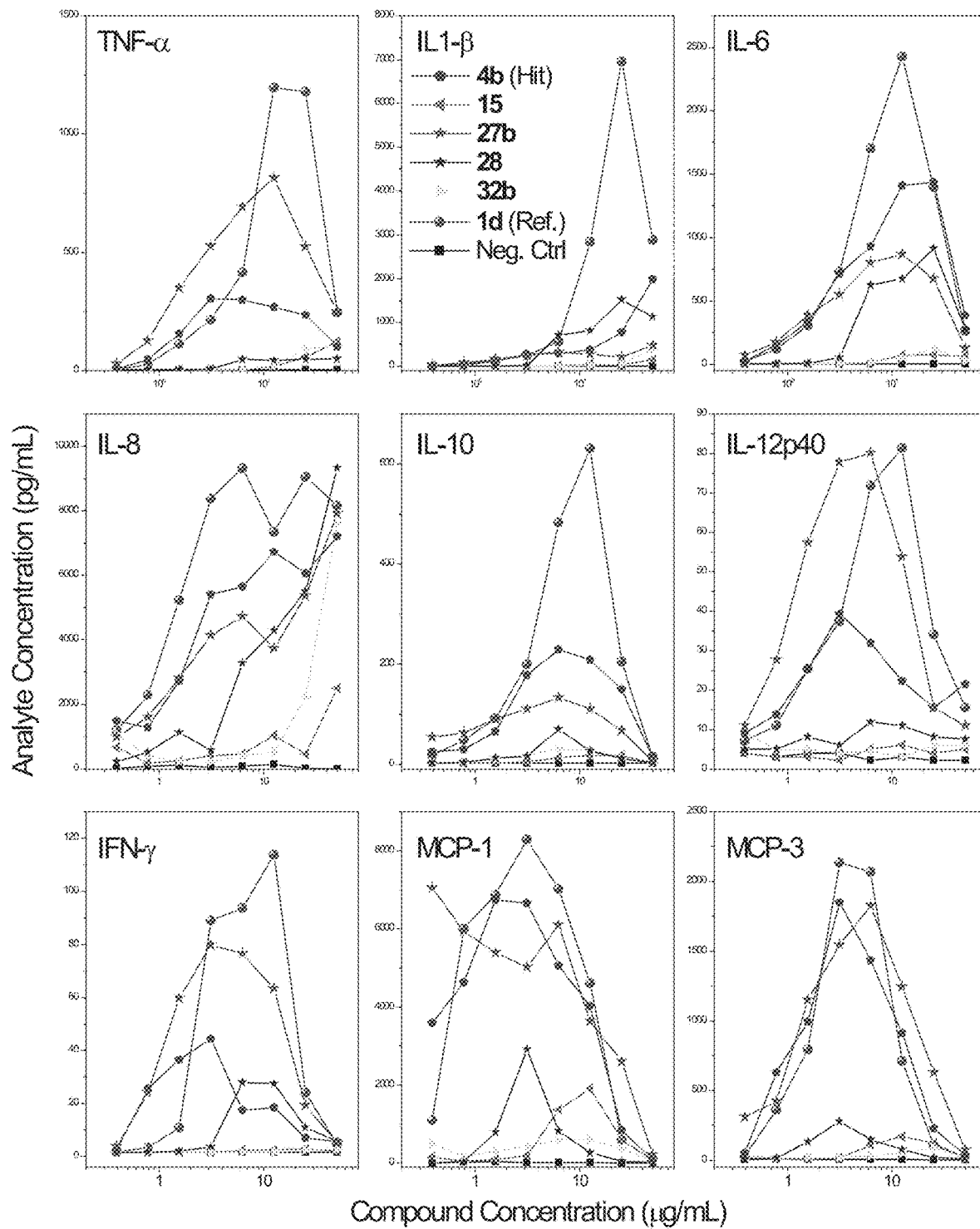
FIG. 3 is a collection of plots of various analyte (e.g., TNF-α, IL-1-β, IL-6, etc.) concentrations as a function of compound concentration.

The hit compound 4b was screened, alongside the 6-methyl analogue 15, the 5-butylamino analogue 27b, the 6-phenyl substituted 28, and its 5-butylamine derivative 32b, for cytokine and chemokine induction in human PBMCs using a 41-analyte multiplexed immunoassay platform. TLR8 agonists upregulate the production of proinflammatory cytokines such as TNF-α, IL-1β, IL-8, as well as a number of chemokines; in addition, TLR8 agonists appear particularly potent in inducing the Th1-biasing cytokines IFN-γ and IL-12. As depicted in FIG. 3, 27b induces a cytokine/chemokine signature prototypical of TLR8 agonists in ex vivo human blood stimulation experiments, the potency ($EC_{50}$: 3 µg/mL; 9.26 µM for TNF-α) of which exceeds that of the benzimidazole 1d (used as a comparator/reference compound). Compound 27b was also found to be particularly potent in inducing Th1-biasing IFN-α and IL-12, while the levels of the proinflammatory cytokines IL-1β, IL-6 and IL-8 appear considerably lower than those observed for 1d (FIG. 3). A cytokine profile characterized by an apparent dissociation between strong IFN-γ, IL-12 and chemokine responses had not been observed on the one hand, and considerably weaker IL-1β, IL-6 and IL-8 levels on the other. These results suggest that the inflammatory and reactogenic propensities of 27b could be considerably more favorable than other TLR8 agonists that are currently being examined in detail in preclinical studies. Notably, the C6-phenyl substituted analogues 28 and 32b are significantly weaker than both the hit compound 4b, as well as the best-in-class aminopyrimidine 27b. An apparent dissociation of activity in primary cell-based reporter assays and secondary screens in human PBMCs have been observed, and the basis for why the C6-phenyl substituted analogues 28 and 32b are active in primary screens, and become highly attenuated in human PBMCs remains to be elucidated.

Figure 4:
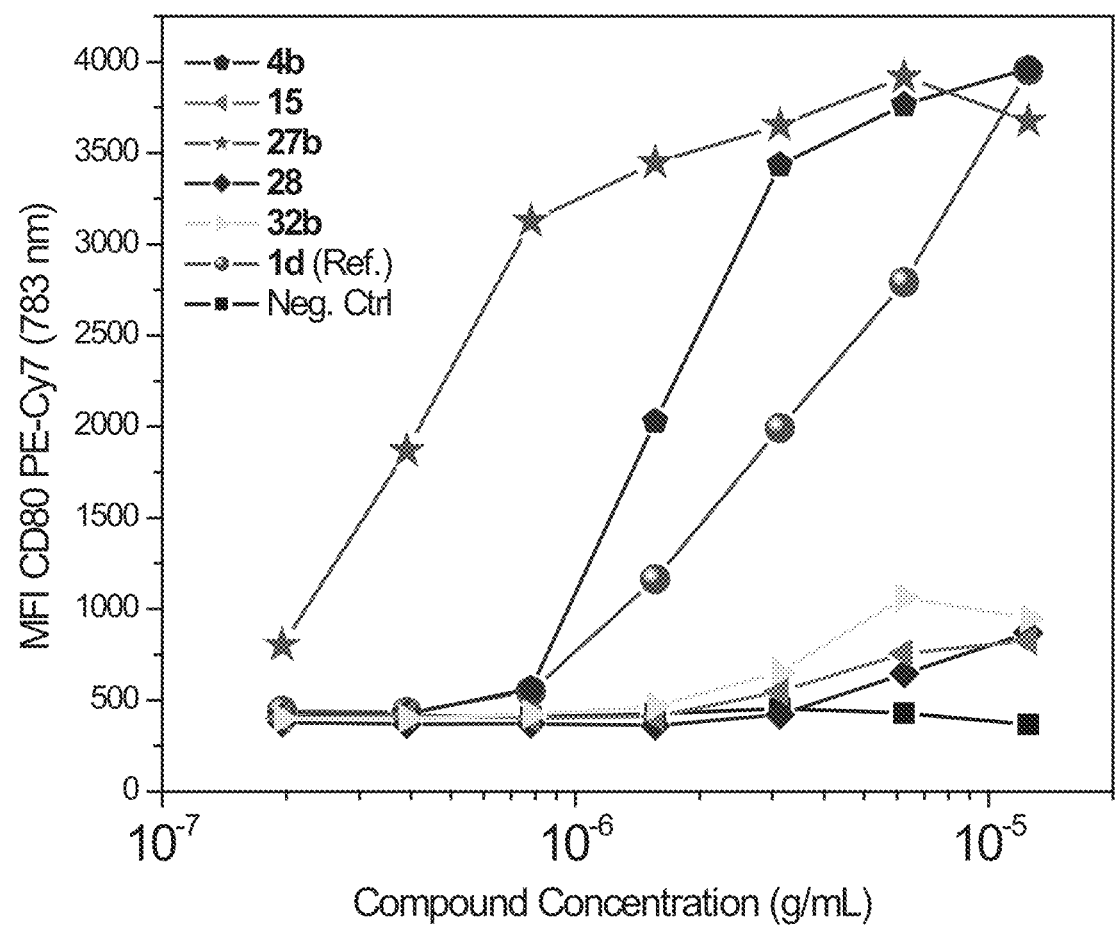
FIG. 4 is a plot of MFI CD80 PE-Cy7 measured at 783 nm as a function of compound concentration.

In an effort to understand the mechanistic basis of amplified adaptive immune functions resulting from TLR8 engagement, multi-color flow cytometry had been used to interrogate activation markers (CD40, CD80) in major cellular subsets (granulocytes, monocytes ($CD14^+$), T cells ($CD3^+$), B cells ($CD19^+$), NK cells ($CD3^-CD56^+$) and cytokine-induced killer cells ($CD3^+CD56^+$) in human whole blood; it had been shown that TLR8 stimulation strongly induces CD80 expression in the monocytes, signifying a possible specific role for TLR8 agonists in enhancing antigen presentation. CD80 responses were examined by the aminopyrimidine compounds. As depicted in FIG. 4, the hit compound 4b, itself, was more active (1.5 µg/mL; 5 µM) than 1d (3 µg/mL; 14 µM in upregulating CD80, and 27b was very potent (0.5 µg/mL; 1.5 µM).

The activation of TLRs by cognate ligands culminates in the recruitment of cytosolic Toll/interleukin-1 receptor (TIR) domain-containing adaptors coupling TLRs to downstream effector proteins. Five adaptors have thus far been identified in signaling: Myeloid differentiation primary response gene 88 (MyD88), MyD88-adapter-like (MAL), TIR-domain-containing adapter-inducing interferon-β (TRIF), TRIF-related adaptor molecule (TRAM) and Sterile-alpha and Armadillo motif containing protein (SARM). These adaptors are thought to converge on either MyD88- or TRIF-dependent pathways leading to the production of inflammatory cytokines (Myd88-dependent), or IFNα/β (TRIF-dependent). The structural features in small-molecule ligands that govern the recruitment of downstream signaling pathways is not understood as yet, and results indicating strong IFN-γ, IL-12, and chemokine responses and weaker proinflammatory responses by 27b suggest that selective targeting of these signaling pathways may be a tractable goal in this chemotype, amenable to classic medicinal chemistry approaches. These finds have been instructive, and efforts are currently underway to further explore substitutions at C5 and C6.

Example 2
Compounds described herein can be synthesized according to the synthetic methods depicted in Schemes 5-8:
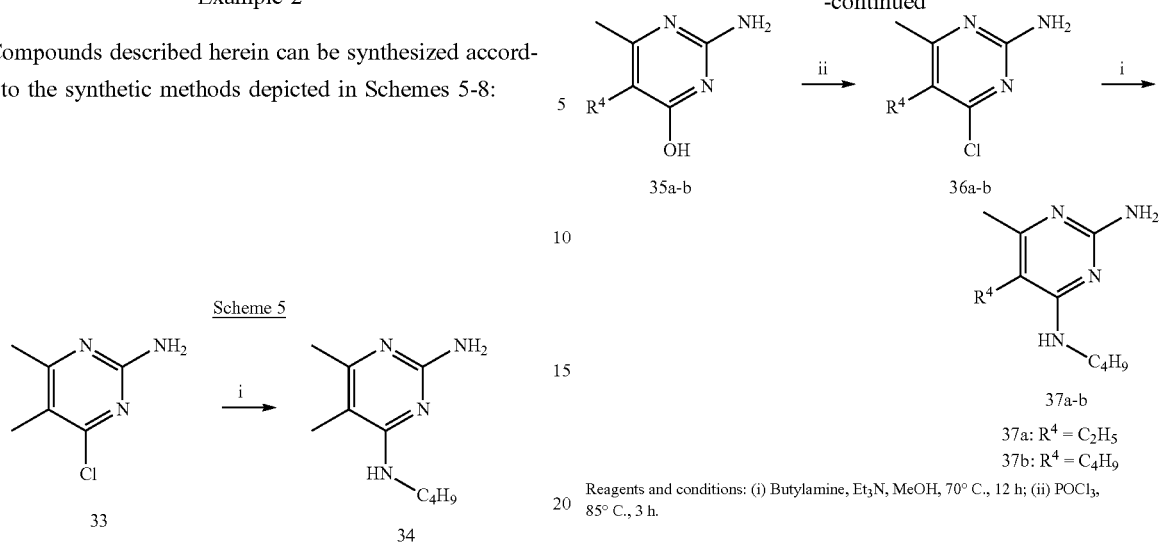
Scheme 5
37a: R⁴ = C₂H₅
37b: R⁴ = C₄H₉
Reagents and conditions: (i) Butylamine, Et₃N, MeOH, 70° C., 12 h; (ii) POCl₃, 85° C., 3 h.
Scheme 6
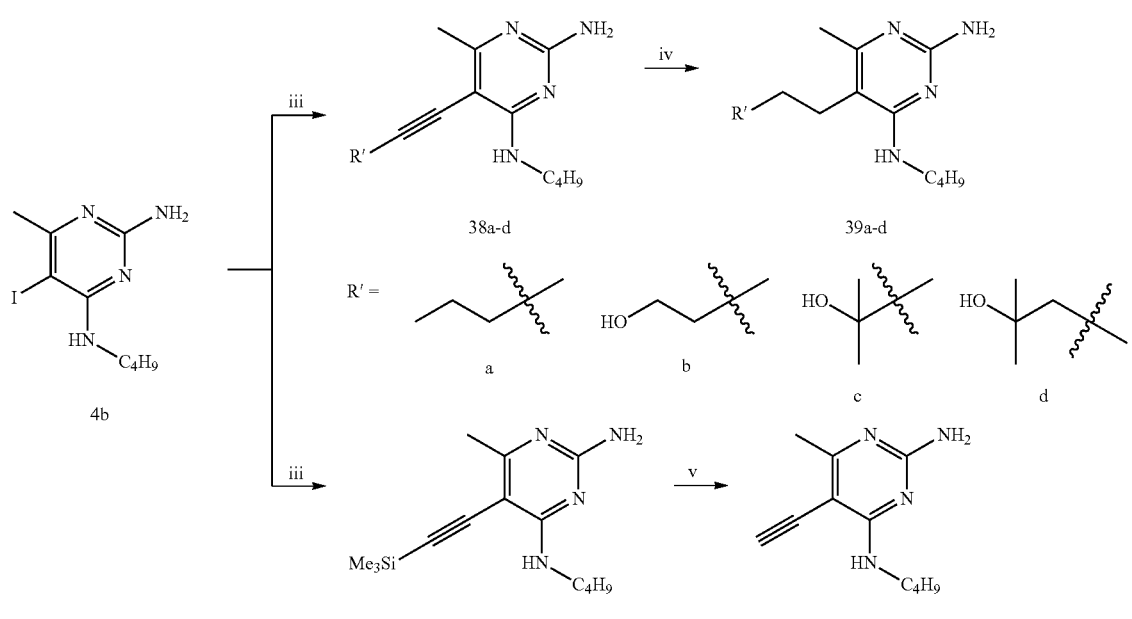
Reagents and conditions: (i) Butylamine, Et₃N, MeOH, 70° C., 12 h; (ii) NIS, DMF, 12 h; (iii) alkyne, Pd(PPh₃)₄, CuI, DIPEA/DMF (1:2), 12 h; (iv) H₂, Pd/C, EtOAc, 50 psi, 5 h; (v) K₂CO₃, MeOH, 3 h.

Scheme 7
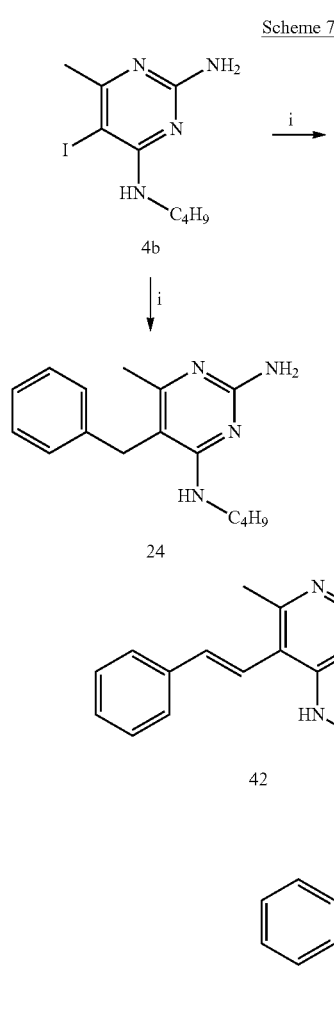
Reagents and conditions: (i) Benzylboronic acid pinacol ester, (for 24) or trans-2-phenylvinylboronic acid (for 43), Pd(dppf)Cl₂, K₂CO₃, 1,4-dioxane/water (4:1), 85° C., 12 h; (ii) H₂, Pd/C, EtOAc, 50 psi, 5 h.
Scheme 8
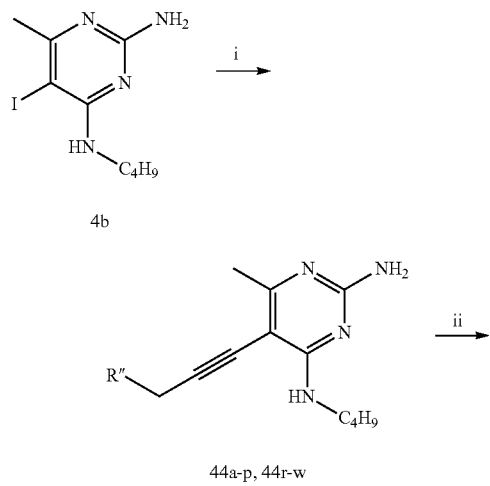
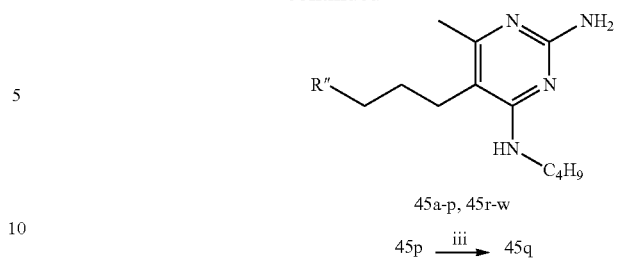
(i) Alkyne, Pd(PPh₃)₄, CuI, DIPEA/DMF (1:2), 12 h; (ii) H₂, Pd/C, EtOAc, 50 psi, 5 h; (iii) HCl, 4M, 3 h.
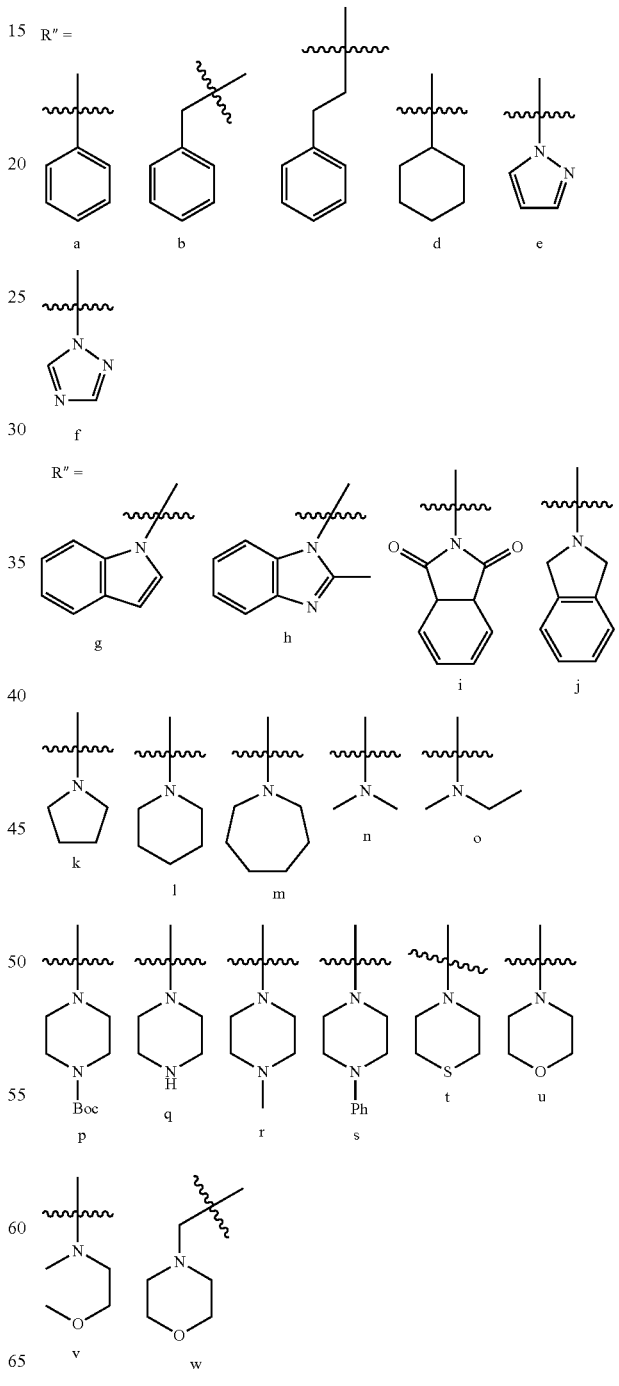

N⁴-Butyl-5,6-dimethylpyrimidine-2,4-diamine (34)

To a solution of compound 33 (31.5 mg, 0.2 mmol) in MeOH (2 mL), were added Et$_3$N (56 µL, 0.4 mmol) and butylamine (39.5 µL, 0.4 mmol). The reaction mixture was stirred for 12 h at 70° C. The reaction mixture was cooled to room temperature and the solvent was removed under reduced pressure, and the crude material was purified by flash chromatography (10% MeOH/CH$_2$Cl$_2$) to afford the compound 34 as a white solid (30 mg, 77%). $^1$H NMR (500 MHz, CDCl$_3$) δ 4.59 (s, 2H), 4.36 (s, 1H), 3.43-3.35 (m, 2H), 2.20 (s, 3H), 1.87 (s, 3H), 1.60-1.51 (m, 2H), 1.44-1.32 (m, 2H), 0.93 (t, J=7.4 Hz, 3H). $^{13}$C NMR (126 MHz, CDCl$_3$) δ 161.9, 161.1, 160.6, 100.7, 40.9, 32.0, 21.7, 20.3, 14.0, 10.9. MS (ESI-QTOF) for C$_{10}$H$_{18}$N$_4$[M+H]$^+$ calculated 195.1604, found 195.1597.

N⁴-Butyl-5-ethyl-6-methylpyrimidine-2,4-diamine (37a)

A suspension of compound 35a (153 mg, 1 mmol) in phosphorus(V) oxychloride (3 mL) was placed in a pressure vessel. The reaction mixture was stirred for 3 h at 85° C. The reaction mixture was cooled to room temperature and the solvent was removed under reduced pressure. The reaction mixture was diluted with water and extracted with EtOAc (3×30 mL). The combined organic layer was dried over Na$_2$SO$_4$ and concentrated under reduced pressure, and the crude material was purified by flash chromatography (60% EtOAc/hexanes) to afford the compound 36a as a white solid (95 mg, 55%). MS (ESI-QTOF) for C$_7$H$_{10}$ClN$_3$ [M+H]$^+$ calculated 172.0636, found 172.0592. To a solution of 36a (34.2 mg, 0.2 mmol) in MeOH (2 mL), was added Et$_3$N (56 µL, 0.4 mmol) and butylamine (39.5 µL, 0.4 mmol). The reaction mixture was stirred for 12 h at 70° C. The reaction mixture was cooled to room temperature and the solvent was removed under reduced pressure, and the crude material was purified by flash chromatography (10% MeOH/CH$_2$Cl$_2$) to afford the compound 37a as a white solid (26 mg, 62%). $^1$H NMR (500 MHz, CDCl$_3$) δ 4.63 (s, 2H), 4.50 (s, 1H), 3.45-3.37 (m, 2H), 2.35 (q, J=7.6 Hz, 2H), 2.22 (s, 3H), 1.62-1.52 (m, 2H), 1.45-1.34 (m, 2H), 1.06 (t, J=7.6 Hz, 3H), 0.95 (t, J=7.4 Hz, 3H). $^{13}$C NMR (126 MHz, CDCl$_3$) δ 161.4, 160.3, 160.2, 107.2, 40.9, 32.0, 20.9, 20.3, 18.8, 14.0, 12.8. MS (ESI-QTOF) for C$_{11}$H$_{20}$N$_4$[M+H]$^+$ calculated 209.1761, found 209.1757.

Compound 37b was synthesized similarly as compound 37a.

N⁴,5-Dibutyl-6-methylpyrimidine-2,4-diamine (37b)

Intermediate compound 36b. Compound 35b was used as reagent. White solid (88 mg, 44%). MS (ESI-QTOF) for C9H$_{14}$ClN$_3$ [M+H]$^+$ calculated 200.0949, found 200.0905.

Compound 37b. White solid (30 mg, 63%). $^1$H NMR (500 MHz, MeOD) δ 3.37 (t, J=7.2 Hz, 2H), 2.37 (t, J=6.5 Hz, 2H), 2.15 (s, 3H), 1.62-1.52 (m, 2H), 1.43-1.32 (m, 6H), 0.99-0.92 (m, 6H). $^{13}$C NMR (126 MHz, MeOD) δ 163.0, 161.9, 160.8, 107.1, 41.5, 32.8, 32.0, 25.7, 23.7, 21.2, 20.6, 14.4, 14.3. MS (ESI-QTOF) for C$_{13}$H$_{24}$N$_4$[M+H]$^+$ calculated 237.2074, found 237.2066.

N⁴-Butyl-6-methylpyrimidine-2,4-diamine (15)

To a solution of compound 2 (574.4 mg, 4 mmol) in MeOH (15 mL), was added Et$_3$N (1120 µL, 8 mmol) and butylamine (790.6 µL, 8 mmol). The reaction mixture was stirred for 12 h at 70° C. The reaction mixture was cooled to room temperature and the solvent was removed under reduced pressure, and the crude material was purified by flash chromatography (10% MeOH/CH$_2$Cl$_2$) to afford the compound 15 as a white solid (540 mg, 75%). $^1$H NMR (500 MHz, CDCl$_3$) δ 5.61 (s, 1H), 4.81 (s, 2H), 4.72 (s, 1H), 3.24-3.16 (m, 2H), 2.18 (s, 3H), 1.58-1.49 (m, 2H), 1.43-1.31 (m, 2H), 0.92 (t, J=7.3 Hz, 3H). $^{13}$C NMR (126 MHz, CDCl$_3$) δ 166.3, 164.1, 162.8, 93.1, 41.2, 31.7, 24.0, 20.2, 13.9. MS (ESI-QTOF) for C$_9$H$_{16}$N$_4$ [M+H]$^+$ calculated 181.1448, found 181.1442.

N⁴-Butyl-5-iodo-6-methylpyrimidine-2,4-diamine (4b)

To a solution of compound 15 (360 mg, 2 mmol) in anhydrous DMF (5 mL) was added NIS (450 mg, 2 mmol), and the reaction mixture was stirred for 12 h. The reaction mixture was diluted with water and extracted with EtOAc (3×50 mL). The combined organic layer was dried over Na$_2$SO$_4$, concentrated under reduced pressure, and the crude material was purified by flash chromatography (70% EtOAc/hexanes) to obtain the compound 4b as a white solid (520 mg, 85%). $^1$H NMR (500 MHz, CDCl$_3$) δ 5.24 (s, 1H), 4.76 (s, 2H), 3.42-3.34 (m, 2H), 2.40 (s, 3H), 1.63-1.53 (m, 2H), 1.44-1.34 (m, 2H), 0.95 (t, J=7.4 Hz, 3H). $^{13}$C NMR (126 MHz, CDCl$_3$) δ 166.5, 162.2, 161.0, 68.5, 41.6, 31.6, 28.8, 20.3, 14.0. MS (ESI-QTOF) for C$_8$H$_{15}$IN$_4$ [M+H]$^+$ calculated 307.0414, found 307.0408.

N⁴-Butyl-6-methyl-5-pentylpyrimidine-2,4-diamine (39a)

To a solution of compound 4b (61.2 mg, 0.2 mmol) in 2:1 mixture of DMF (2 mL) and DIPEA (1 mL) were added Pd(PPh$_3$)$_4$ (23.1 mg, 0.02 mmol) and CuI (7.6 mg, 0.04 mmol). The reaction mixture was degassed with dry nitrogen for 5 min, then 1-pentyne (39.4 µL, 0.4 mmol) was added. The resulting reaction mixture was stirred for 12 h under nitrogen atmosphere. After completion of the reaction, the mixture was diluted with water and extracted with ethylacetate (3×20 mL). The combined organic layer was dried over Na$_2$SO$_4$ and concentrated under reduced pressure, the crude material was purified by flash chromatography (90% EtOAc/hexanes) to obtain the compound 38a as yellow oil (38 mg, 77%). $^1$H NMR (500 MHz, CDCl$_3$) δ 5.36 (s, 1H), 4.76 (s, 2H), 3.44-3.36 (m, 2H), 2.46 (t, J=6.9 Hz, 2H), 2.31 (s, 3H), 1.69-1.52 (m, 4H), 1.45-1.34 (m, 2H), 1.05 (t, J=7.4 Hz, 3H), 0.95 (t, J=7.3 Hz, 3H). $^{13}$C NMR (126 MHz, CDCl$_3$) δ 166.7, 163.1, 160.5, 99.7, 92.1, 74.0, 40.5, 31.9, 22.8, 22.6, 22.0, 20.2, 14.0, 13.7. MS (ESI-QTOF) for C$_{14}$H$_{22}$N$_4$ [M+H]$^+$ calculated 247.1917, found 247.1939. To a solution of compound 38a (24.6 mg, 0.1 mmol) in anhydrous EtOAc (10 mL) was added a catalytic amount of Pd/C, and the reaction mixture was subjected to hydrogenation at 50 psi for 5 h. The reaction mixture was filtered, and the filtrate was concentrated under reduced pressure. The crude material was purified by flash chromatography (10% MeOH/CH$_2$Cl$_2$) to obtain the compound 39a as a pale oil (20 mg, 80%). $^1$H NMR (500 MHz, MeOD) δ 3.38 (t, J=7.2 Hz, 2H), 2.37 (t, J=7.6 Hz, 2H), 2.16 (s, 3H), 1.62-1.52 (m, 2H), 1.46-1.32 (m, 8H), 0.98-0.90 (m, 6H). $^{13}$C NMR (126 MHz, MeOD) δ 163.1, 161.5, 160.2, 107.2, 41.5, 32.8, 32.7, 29.4, 25.8, 23.8, 21.2, 20.4, 14.4, 14.3. MS (ESI-QTOF) for C$_{14}$H$_{26}$N$_4$ [M+H]$^+$ calculated 251.2230, found 251.2228.

Compounds 39b-d were synthesized similarly as compound 39a.

4-(2-Amino-4-(butylamino)-6-methylpyrimidin-5-yl)butan-1-ol (42b)

Intermediate compound 38b. But-3-yn-1-ol was used as reagent. Yellow solid (40 mg, 80%). MS (ESI-QTOF) for $C_{13}H_{20}N_4O$ [M+H]$^+$ calculated 249.1710, found 249.1689.

Compound 39b. White solid (20 mg, 79%). $^1$H NMR (500 MHz, MeOD) δ 3.60 (t, J=6.4 Hz, 2H), 3.38 (t, J=7.2 Hz, 2H), 2.41 (t, J=8.0 Hz, 2H), 2.17 (s, 3H), 1.63-1.55 (m, 4H), 1.52-1.46 (m, 2H), 1.42-1.34 (m, 2H), 0.95 (t, J=7.4 Hz, 3H). $^{13}$C NMR (126 MHz, MeOD) δ 163.1, 161.7, 160.4, 107.1, 62.7, 41.6, 32.9, 32.7, 26.0, 25.5, 21.2, 20.4, 14.3. MS (ESI-QTOF) for C13H$_{24}$N$_4$O [M+H]$^+$ calculated 253.2023, found 253.2011.

4-(2-Amino-4-(butylamino)-6-methylpyrimidin-5-yl)-2-methylbutan-2-ol (39c)

Intermediate compound 38c. 2-Methylbut-3-yn-2-ol was used as reagent. Yellow solid (42 mg, 80%). MS (ESI-QTOF) for $Cl_4H_{22}N_4O$ [M+H]$^+$ calculated 263.1866, found 263.1868.

Compound 39c. White solid (20 mg, 75%). $^1$H NMR (500 MHz, MeOD) δ 3.38 (t, J=7.2 Hz, 2H), 2.47-2.40 (m, 2H), 2.16 (s, 3H), 1.61-1.55 (m, 2H), 1.53-1.49 (m, 2H), 1.44-1.37 (m, 2H), 1.26 (s, 6H), 0.96 (t, J=7.4 Hz, 3H). $^{13}$C NMR (126 MHz, MeOD) δ 162.9, 161.8, 160.3, 107.1, 71.2, 42.4, 41.6, 32.6, 29.3, 21.3, 20.5, 20.3, 14.2. MS (ESI-QTOF) for $C_{14}H_{26}N_4O$ [M+H]$^+$ calculated 267.2179, found 267.2177.

5-(2-Amino-4-(butylamino)-6-methylpyrimidin-5-yl)-2-methylpentan-2-ol (39d)

Intermediate compound 38d. 2-Methylpent-4-yn-2-ol was used as reagent. Yellow oil (46 mg, 83%). MS (ESI-QTOF) for $C_{15}H_{24}N_4O$ [M+H]$^+$ calculated 277.2023, found 277.2029.

Compound 39d. White solid (22 mg, 78%). $^1$H NMR (500 MHz, MeOD) δ 3.38 (t, J=7.1 Hz, 2H), 2.42-2.36 (m, 2H), 2.16 (s, 3H), 1.61-1.54 (m, 2H), 1.53-1.49 (m, 4H), 1.42-1.34 (m, 2H), 1.17 (s, 6H), 0.95 (t, J=7.4 Hz, 3H). $^{13}$C NMR (126 MHz, MeOD) δ 163.1, 161.8, 160.8, 107.0, 71.4, 43.9, 41.5, 32.8, 29.3, 26.3, 24.3, 21.2, 20.6, 14.3. MS (ESI-QTOF) for $C_{15}H_{28}N_4O$ [M+H]$^+$ calculated 281.2336, found 281.2336.

N$^4$-Butyl-5-ethynyl-6-methylpyrimidine-2,4-diamine (41)

To a solution of compound 4b (92 mg, 0.3 mmol) in 2:1 mixture of DMF (3 mL) and DIPEA (1.5 mL) were added Pd(PPh$_3$)$_4$ (34.6 mg, 0.03 mmol) and CuI (11.4 mg, 0.06 mmol). The reaction mixture was degassed with dry nitrogen for 5 min, then ethynyltrimethylsilane (83 μL, 0.6 mmol) was added. The resulting reaction mixture was stirred for 12 h under nitrogen atmosphere. After completion of the reaction, the mixture was diluted with water and extracted with ethylacetate (3×30 mL). The combined organic layer was dried over Na$_2$SO$_4$ and concentrated under reduced pressure, the crude material was purified by flash chromatography (50% EtOAc/hexanes) to obtain the compound 40 as white solid (63 mg, 76%). $^1$H NMR (500 MHz, CDCl$_3$) δ 5.39 (s, 1H), 4.91 (s, 2H), 3.45-3.37 (m, 2H), 2.33 (s, 3H), 1.62-1.52 (m, 2H), 1.46-1.35 (m, 2H), 0.96 (t, J=7.4 Hz, 3H), 0.25 (s, 9H). $^{13}$C NMR (126 MHz, CDCl$_3$) δ 167.9, 163.3, 160.8, 104.4, 99.3, 91.4, 40.5, 31.8, 22.9, 20.2, 14.0, 0.3. MS (ESI-QTOF) for $C_{14}H_{24}N_4Si$ [M+H]$^+$ calculated 277.1843, found 277.1816. To a solution of 40 (27.6 mg, 0.1 mmol) in MeOH (2 mL) was added K$_2$CO$_3$ (13.8 g, 0.1 mmol). The reaction mixture was stirred for 3 h. After completion of the reaction, the mixture was diluted with water and extracted with ethylacetate (3×20 mL). The combined organic layer was dried over Na$_2$SO$_4$ and concentrated under reduced pressure, the crude material was purified by flash chromatography (50% EtOAc/hexanes) to obtain the compound 41 as yellow oil (14 mg, 69%). $^1$H NMR (500 MHz, CDCl$_3$) δ 5.39 (s, 1H), 4.92 (s, 2H), 3.61 (s, 1H), 3.45-3.37 (m, 2H), 2.34 (s, 3H), 1.62-1.52 (m, 2H), 1.45-1.33 (m, 2H), 0.95 (t, J=7.4 Hz, 3H). $^{13}$C NMR (126 MHz, CDCl$_3$) δ 168.3, 163.5, 161.0, 90.1, 87.0, 78.1, 40.6, 31.8, 22.8, 20.2, 14.0. MS (ESI-QTOF) for $C_{11}H_{16}N_4$ [M+H]$^+$ calculated 205.1448, found 205.1445.

N$^4$-Butyl-6-methyl-5-phenethylpyrimidine-2,4-diamine (43)

To a solution of compound 4b (61.2 mg, 0.2 mmol), trans-2-phenylvinylboronic acid (44.4 mg, 0.3 mmol) and K$_2$CO$_3$ (83 mg, 0.6 mmol) in 4:1 mixture of 1,4-dioxane (3 mL) and water (0.75 mL) was added Pd(dppf)Cl$_2$ (11 mg, 0.015 mmol). The reaction mixture was degassed with dry nitrogen for 5 min, then stirred for 12 h at 85° C. under nitrogen atmosphere. The reaction mixture was diluted with water and extracted with EtOAc (3×20 mL). The combined organic layer was dried over Na$_2$SO$_4$, concentrated under reduced pressure, and the crude material was purified by flash chromatography (10% MeOH/CH$_2$Cl$_2$) to obtain the compound 42 as a yellow oil (44 mg, 78%). MS (ESI-QTOF) for $C_{17}H_{22}N_4$ [M+H]$^+$ calculated 283.1917, found 283.1890. To a solution of compound 42 (28.2 mg, 0.1 mmol) in anhydrous EtOAc (10 mL) was added a catalytic amount of Pd/C, and the reaction mixture was subjected to hydrogenation at 50 psi for 5 h. The reaction mixture was filtered, and the filtrate was concentrated under reduced pressure. The crude material was purified by flash chromatography (10% MeOH/CH$_2$Cl$_2$) to obtain the compound 43 as a white solid (20 mg, 70%). $^1$H NMR (500 MHz, MeOD) δ 7.24-7.21 (m, 2H), 7.17-7.14 (m, 1H), 7.11 (d, J=7.4 Hz, 2H), 3.35 (t, J=7.2 Hz, 2H), 2.77-2.65 (m, 4H), 1.84 (s, 3H), 1.60-1.50 (m, 2H), 1.44-1.32 (m, 2H), 0.96 (t, J=7.4 Hz, 3H). $^{13}$C NMR (126 MHz, MeOD) δ 163.1, 161.9, 161.6, 142.8, 129.9, 129.3, 127.0, 105.8, 41.6, 35.4, 32.8, 28.0, 21.3, 20.4, 14.3. MS (ESI-QTOF) for $C_{17}H_{24}N_4$[M+H]$^+$ calculated 285.2074, found 285.2065.

Compounds 45a-p were synthesized similarly as compound 39a.

N$^4$-Butyl-6-methyl-5-(3-phenylpropyl)pyrimidine-2,4-diamine (45a)

Intermediate compound 44a. Prop-2-yn-1-ylbenzene was used as reagent. Yellow solid (46 mg, 78%). $^1$H NMR (500 MHz, MeOD) δ 7.42-7.40 (m, 2H), 7.35-7.31 (m, 2H), 7.25-7.22 (m, 1H), 3.91 (s, 2H), 3.39 (t, J=7.1 Hz, 2H), 2.27 (s, 3H), 1.57-1.51 (m, 2H), 1.39-1.31 (m, 2H), 0.94 (t, J=7.4 Hz, 3H). $^{13}$C NMR (126 MHz, MeOD) δ 166.8, 164.3, 162.1, 138.7, 129.6, 128.9, 127.7, 98.6, 92.3, 76.1, 41.3, 32.8, 26.7, 22.3, 21.1, 14.2. MS (ESI-QTOF) for $C_{18}H_{22}N_4$ [M+H]$^+$ calculated 295.1917, found 295.1941.

Compound 45a. Pale oil (23 mg, 77%). $^1$H NMR (500 MHz, MeOD) δ 7.29-7.25 (m, 2H), 7.22-7.15 (m, 3H), 3.36

(t, J=7.1 Hz, 2H), 2.68 (t, J=7.5 Hz, 2H), 2.38 (t, J=8.0 Hz, 2H), 2.07 (s, 3H), 1.77-1.67 (m, 2H), 1.58-1.49 (m, 2H), 1.41-1.29 (m, 2H), 0.95 (t, J=7.4 Hz, 3H). $^{13}$C NMR (126 MHz, MeOD) δ 163.0, 161.5, 160.1, 143.5, 129.5, 129.4, 126.9, 106.8, 41.6, 36.5, 32.7, 31.4, 25.2, 21.2, 20.2, 14.3. MS (ESI-QTOF) for $C_{18}H_{26}N_4$[M+H]$^+$ calculated 299.2230, found 299.2253.

N$^4$-Butyl-6-methyl-5-(4-phenylbutyl)pyrimidine-2,4-diamine (45b)

Intermediate compound 44b. But-3-yn-1-ylbenzene was used as reagent. Yellow solid (48 mg, 78%). MS (ESI-QTOF) for $C_{19}H_{24}N_4$[M+H]$^+$ calculated 309.2074, found 309.2013.

Compound 45b. Pale oil (25 mg, 80%). $^1$H NMR (500 MHz, MeOD) δ 7.26-7.23 (m, 2H), 7.18-7.12 (m, 3H), 3.37 (t, J=7.2 Hz, 2H), 2.64 (t, J=7.6 Hz, 2H), 2.40 (t, J=7.9 Hz, 2H), 2.14 (s, 3H), 1.73-1.67 (m, 2H), 1.56-1.50 (m, 2H), 1.47-1.41 (m, 2H), 1.37-1.31 (m, 2H), 0.93 (t, J=7.4 Hz, 3H). $^{13}$C NMR (126 MHz, MeOD) δ 163.1, 160.9, 159.0, 143.6, 129.4, 129.3, 126.7, 107.2, 41.6, 36.8, 32.7, 32.2, 29.1, 25.5, 21.2, 20.0, 14.3. MS (ESI-QTOF) for $C_{19}H_2N_4$ [M+H]$^+$ calculated 313.2387, found 313.2356.

N$^4$-Butyl-6-methyl-5-(5-phenylpentyl)pyrimidine-2,4-diamine (45c)

Intermediate compound 44c. Pent-4-yn-1-ylbenzene was used as reagent. Yellow oil (50 mg, 78%). MS (ESI-QTOF) for $C_{20}H_{26}N_4$ [M+H]$^+$ calculated 323.2230, found 323.2261.

Compound 45c. Pale oil (25 mg, 76%). $^1$H NMR (500 MHz, MeOD) δ 7.25-7.21 (m, 2H), 7.15-7.11 (m, 3H), 3.38 (t, J=7.2 Hz, 2H), 2.61 (t, J=7.6 Hz, 2H), 2.37 (t, J=7.5 Hz, 2H), 2.14 (s, 3H), 1.67-1.61 (m, 2H), 1.59-1.53 (m, 2H), 1.47-1.33 (m, 6H), 0.95 (t, J=7.4 Hz, 3H). $^{13}$C NMR (126 MHz, MeOD) δ 163.1, 161.2, 159.6, 143.8, 129.4, 129.3, 126.7, 107.2, 41.6, 36.8, 32.8, 32.7, 30.0, 29.5, 25.7, 21.2, 20.2, 14.3. MS (ESI-QTOF) for $C_{20}H_{30}N_4$ [M+H]$^+$ calculated 327.2543, found 327.2581.

N$^4$-Butyl-5-(3-cyclohexylpropyl)-6-methylpyrimidine-2,4-diamine (45d)

Intermediate compound 44d. Prop-2-yn-1-ylcyclohexane was used as reagent. Yellow solid (48 mg, 80%). MS (ESI-QTOF) for $C_{18}H_{28}N_4$ [M+H]$^+$ calculated 301.2387, found 301.2384.

Compound 45d. White solid (25 mg, 82%). $^1$H NMR (500 MHz. MeOD) b 3.40 (t, J=7.1 Hz, 2H), 2.36 (t, J=7.7 Hz, 2H), 2.16 (s, 3H), 1.74-1.64 (m, 5H), 1.60-1.54 (m, 2H), 1.47-1.34 (m, 4H), 1.30-1.15 (m, 6H), 0.95 (t, J=7.4 Hz, 3H), 0.92-0.86 (m, 2H). $^{13}$C NMR (126 MHz, MeOD) δ 163.1, 161.0, 159.2, 107.4, 41.6, 39.1, 38.3, 34.6, 32.7, 27.8, 27.5, 26.9, 25.9, 21.2, 20.1, 14.3. MS (ESI-QTOF) for $C_{18}H_{32}N_4$ [M+H]$^+$ calculated 305.2700, found 305.2711.

5-(3-(1H-Pyrazol-1-yl)propyl)-N$^4$-butyl-6-methylpyrimidine-2,4-diamine (45e)

Intermediate compound 44e. 1-(Prop-2-yn-1-yl)-1H-pyrazole was used as reagent. Pale yellow solid (40 mg, 70%). MS (ESI-QTOF) for $C_{15}H_{20}N_6$ [M+H]$^+$ calculated 285.1822, found 285.1822.

Compound 45e. White solid (16 mg, 55%). $^1$H NMR (500 MHz, CDCl$_3$) δ 7.56 (d, J=1.4 Hz, 1H), 7.42 (d, J=2.2 Hz, 1H), 6.31-6.30 (m, 1H), 5.83 (s, 1H), 4.59 (s, 2H), 4.16 (t, J=5.8 Hz, 2H), 3.41-3.37 (m, 2H), 2.34 (t, J=7.7 Hz, 2H), 2.19 (s, 3H), 2.06-2.00 (m, 2H), 1.62-1.56 (m, 2H), 1.42-1.35 (m, 2H), 0.95 (t, J=7.3 Hz, 3H). $^{13}$C NMR (126 MHz, CDCl$_3$) δ 162.0, 160.7, 160.6, 139.5, 130.1, 105.7, 104.8, 50.8, 41.0, 31.7, 28.2, 22.6, 21.1, 20.4, 14.1. MS (ESI-QTOF) for $C_{15}H_{24}N_6$ [M+H]$^+$ calculated 289.2135, found 289.2138.

5-(3-(1H-1,2,4-Triazol-1-yl)propyl)-M-butyl-6-methylpyrimidine-2,4-diamine (45f)

Intermediate compound 44f. 1-(Prop-2-yn-1-yl)-1H-1,2,4-triazole was used as reagent. Yellow solid (45 mg, 79%). MS (ESI-QTOF) for $C_{14}H_{19}N_7$[M+H]$^+$ calculated 286.1775, found 286.1776.

Compound 45f. White solid (22 mg, 76%). $^1$H NMR (500 MHz, MeOD) δ 8.47 (s, 1H), 8.03 (s, 1H), 4.30 (t, J=6.8 Hz, 2H), 3.39 (t, J=7.1 Hz, 2H), 2.40 (t, J=7.9 Hz, 2H), 2.10 (s, 3H), 2.03-1.96 (m, 2H), 1.62-1.56 (m, 2H), 1.42-1.34 (m, 2H), 0.96 (t, J=7.4 Hz, 3H). $^{13}$C NMR (126 MHz, MeOD) δ 163.1, 162.2, 161.4, 152.2, 145.2, 105.3, 49.9, 41.6, 32.7, 29.2, 23.0, 21.3, 20.4, 14.3. MS (ESI-QTOF) for $C_{14}H_{23}N_7$ [M+H]$^+$ calculated 290.2088, found 290.2092.

5-(3-(1H-Indol-1-yl)propyl)-M-butyl-6-methylpyrimidine-2,4-diamine (45g)

Intermediate compound 44g. 1-(Prop-2-yn-1-yl)-1H-indole was used as reagent. Yellow oil (50 mg, 75%). MS (ESI-QTOF) for $C_{20}H_{23}N_5$ [M+H]$^+$ calculated 334.2026, found 334.2027.

Compound 45g. White solid (24 mg, 71%). $^1$H NMR (500 MHz, CDCl$_3$) δ 7.66 (d, J=7.9 Hz, 1H), 7.35-7.33 (m, 1H), 7.24-7.20 (m, 1H), 7.14-7.11 (m, 2H), 6.55 (d, J=3.0 Hz, 1H), 4.91 (s, 2H), 4.22 (t, J=6.2 Hz, 2H), 3.84 (s, 1H), 3.07-3.03 (m, 2H), 2.21-2.15 (m, 5H), 1.99-1.93 (m, 2H), 1.18-1.12 (m, 4H), 0.86 (t, J=6.3 Hz, 3H). $^{13}$C NMR (126 MHz, CDCl$_3$) 5161.2, 159.6, 158.9, 135.9, 128.9, 128.0, 122.1, 121.5, 119.9, 109.5, 104.5, 101.8, 46.0, 40.9, 31.4, 28.5, 22.4, 20.3, 20.2, 14.0. MS (ESI-QTOF) for $C_{20}H_{27}N_5$ [M+H]$^+$ calculated 338.2339, found 338.2341.

N$^4$-Butyl-6-methyl-5-(3-(2-methyl-1H-benzo[d]imidazol-1-yl)propyl)pyrimidine-2,4-diamine (45h)

Intermediate compound 44h. 2-Methyl-1-(prop-2-yn-1-yl)-1H-benzo[d]imidazole was used as reagent. Pale yellow solid (50 mg, 72%). MS (ESI-QTOF) for $C_{20}H_{24}N_6$ [M+H]$^+$ calculated 349.2135, found 349.2127.

Compound 45h. White solid (28 mg, 79%). $^1$H NMR (500 MHz, MeOD) δ 7.56 (d, J=8.7 Hz, 1H), 7.44 (d, J=7.5 Hz, 1H), 7.26-7.20 (m, 2H), 4.28 (t, J=7.3 Hz, 2H), 3.35 (t, J=7.2 Hz, 2H), 2.60 (s, 3H), 2.42 (t, J=8.2 Hz, 2H), 2.00 (s, 3H), 1.96-1.86 (m, 2H), 1.56-1.46 (m, 2H), 1.38-1.27 (m, 2H), 0.92 (t, J=7.4 Hz, 3H). $^{13}$C NMR (126 MHz, MeOD) δ 162.9, 162.2, 161.4, 153.2, 142.9, 136.0, 123.5, 123.3, 119.0, 110.9, 105.3, 44.1, 41.5, 32.8, 29.3, 22.9, 21.2, 20.4, 14.3, 13.5. MS (ESI-QTOF) for $C_{20}H_{28}N_6$ [M+H]$^+$ calculated 353.2448, found 353.2446.

2-(3-(2-Amino-4-(butylamino)-6-methylpyrimidin-5-yl)propyl)isoindoline-1,3-dione (45i)

Intermediate compound 44i. 2-(Prop-2-yn-1-yl)isoindoline-1,3-dione was used as reagent. Yellow solid (52 mg, 72%). MS (ESI-QTOF) for $C_{20}H_{21}N_5O_2$ [M+H]$^+$ calculated 364.1768, found 364.1786.

Compound 45i. White solid (28 mg, 76%). $^1$H NMR (500 MHz, MeOD) δ 7.87-7.83 (m, 2H), 7.82-7.79 (m, 2H), 3.74 (t, J=7.2 Hz, 2H), 3.37 (t, J=7.2 Hz, 2H), 2.44 (t, J=8.1 Hz, 2H), 2.13 (s, 3H), 1.84-1.74 (m, 2H), 1.61-1.52 (m, 2H), 1.42-1.31 (m, 2H), 0.94 (t, J=7.3 Hz, 3H). $^{13}$C NMR (126 MHz, MeOD) δ 170.0, 163.0, 161.6, 160.2, 135.4, 133.4, 124.1, 106.0, 41.6, 38.7, 32.7, 28.2, 23.4, 21.2, 20.2, 14.3. MS (ESI-QTOF) for $C_{20}H_{25}N_5O_2[M+H]^+$ calculated 368.2081, found 368.2114.

N$^4$-Butyl-5-(3-(Isoindolin-2-yl)propyl)-6-methylpyrimidine-2,4-diamine (45)

Intermediate compound 44j. 2-(Prop-2-yn-1-yl)isoindoline was used as reagent. Yellow solid (50 mg, 75%). MS (ESI-QTOF) for $C_{20}H_{25}N_5$ $[M+H]^+$ calculated 336.2183, found 336.2192.

Compound 45j. White solid (24 mg, 71%). $^1$H NMR (500 MHz, MeOD) δ 7.28-7.19 (m, 4H), 3.93 (s, 4H), 3.32-3.29 (m, 2H), 2.74 (t, J=6.9 Hz, 2H), 2.51 (t, J=7.2 Hz, 2H), 2.20 (s, 3H), 1.82-1.72 (m, 2H), 1.46-1.36 (m, 2H), 1.33-1.21 (m, 2H), 0.83 (t, J=7.4 Hz, 3H). $^{13}$C NMR (126 MHz, MeOD) δ 163.7, 162.1, 161.4, 140.8, 128.1, 123.3, 106.3, 59.8, 55.4, 41.9, 32.6, 28.4, 23.2, 21.3, 20.6, 14.2. MS (ESI-QTOF) for $C_{20}H_{29}N_5[M+H]^+$ calculated 340.2496, found 340.2506.

N$^4$-Butyl-6-methyl-5-(3-(pyrrolidin-1-yl)propyl) pyrimidine-2,4-diamine (45k)

Intermediate compound 44k. 1-(Prop-2-yn-1-yl)pyrrolidine was used as reagent. Yellow solid (40 mg, 70%). MS (ESI-QTOF) for $C_{16}H_{25}N_5$ $[M+H]^+$ calculated 288.2183, found 288.2163.

Compound 45k. White solid (24 mg, 82%). $^1$H NMR (500 MHz, MeOD) δ 3.38 (t, J=7.2 Hz, 2H), 2.58-2.53 (m, 4H), 2.48 (t, J=7.4 Hz, 2H), 2.43 (t, J=7.5 Hz, 2H), 2.17 (s, 3H), 1.84-1.80 (m, 4H), 1.70-1.64 (m, 2H), 1.60-1.55 (m, 2H), 1.41-1.36 (m, 2H), 0.96 (t, J=7.4 Hz, 3H). $^{13}$C NMR (126 MHz, MeOD) δ 163.5, 161.9, 161.0, 106.4, 56.2, 54.9, 41.7, 32.9, 28.5, 24.2, 23.4, 21.3, 20.5, 14.3. MS (ESI-QTOF) for $C_{16}H_{29}N_5$ $[M+H]^+$ calculated 292.2496, found 292.2494.

N$^4$-Butyl-6-methyl-5-(3-(piperidin-1-yl)propyl)pyrimidine-2,4-diamine (45l)

Intermediate compound 44l. 1-(Prop-2-yn-1-yl)piperidine was used as reagent. Yellow solid (44 mg, 73%). $^1$H NMR (500 MHz, CDCl$_3$) δ 5.37 (s, 1H), 4.75 (s, 2H), 3.57 (s, 2H), 3.45-3.37 (m, 2H), 2.58-2.52 (m, 4H), 2.33 (s, 3H), 1.67-1.62 (m, 4H), 1.60-1.54 (m, 2H), 1.45-1.36 (m, 4H), 0.95 (t, J=7.3 Hz, 3H). $^{13}$C NMR (126 MHz, CDCl$_3$) δ 167.3, 163.2, 160.7, 94.6, 91.4, 78.7, 53.5, 49.0, 40.6, 31.9, 26.1, 24.1, 23.1, 20.3, 14.0. MS (ESI-QTOF) for $C_{17}H_{27}N_5[M+H]^+$ calculated 302.2339, found 302.2346.

Compound 45l. White solid (24 mg, 78%). $^1$H NMR (500 MHz, MeOD) δ 3.39 (t, J=7.2 Hz, 2H), 2.46-2.37 (m, 6H), 2.33 (t, J=7.4 Hz, 2H), 2.16 (s, 3H), 1.67-1.55 (m, 8H), 1.51-1.47 (m, 2H), 1.42-1.36 (m, 2H), 0.95 (t, J=7.4 Hz, 3H). $^{13}$C NMR (126 MHz, MeOD) δ 163.4, 161.9, 161.0, 106.4, 59.1, 55.5, 41.5, 33.0, 26.7, 26.4, 25.3, 23.4, 21.3, 20.5, 14.3. MS (ESI-QTOF) for $C_{17}H_{31}N_5$ $[M+H]^+$ calculated 306.2652, found 306.2664.

5-(3-(Azepan-1-yl)propyl)-M-butyl-6-methylpyrimidine-2,4-diamine (45m)

Intermediate compound 44m. 1-(Prop-2-yn-1-yl)azepane was used as reagent. Pale yellow solid (50 mg, 79%). MS (ESI-QTOF) for $C_{18}H_{29}N_5[M+H]^+$ calculated 316.2496, found 316.2495.

Compound 45m. White solid (24 mg, 75%). $^1$H NMR (500 MHz, CDCl$_3$) δ 6.66 (s, 1H), 4.74 (s, 2H), 3.43-3.35 (m, 2H), 2.67-2.61 (m, 4H), 2.43-2.36 (m, 4H), 2.22 (s, 3H), 1.70-1.62 (m, 10H), 1.58-1.52 (m, 2H), 1.41-1.34 (m, 2H), 0.94 (t, J=7.3 Hz, 3H). $^{13}$C NMR (126 MHz, CDCl$_3$) 163.0, 159.5, 158.8, 106.0, 55.1, 54.3, 41.1, 32.1, 27.3, 27.1, 26.4, 21.9, 20.4, 20.3, 14.1. MS (ESI-QTOF) for $C_{18}H_{33}N_5$ $[M+H]^+$ calculated 320.2809, found 320.2818.

N$^4$-Butyl-5-(3-(dimethylamino)propyl)-6-methylpyrimidine-2,4-diamine (45n)

Intermediate compound 44n. N,N-Dimethylprop-2-yn-1-amine was used as reagent. Yellow solid (38 mg, 73%). MS (ESI-QTOF) for $C_{14}H_{23}N_5$ $[M+H]^+$ calculated 262.2026, found 262.2060.

Compound 45n. White solid (20 mg, 75%). $^1$H NMR (500 MHz, MeOD) δ 3.37 (t, J=7.2 Hz, 2H), 2.41 (t, J=7.5 Hz, 2H), 2.32 (t, J=7.3 Hz, 2H), 2.24 (s, 6H), 2.16 (s, 3H), 1.67-1.53 (m, 4H), 1.45-1.33 (m, 2H), 0.96 (t, J=7.4 Hz, 3H). $^{13}$C NMR (126 MHz, MeOD) δ 163.4, 162.1, 161.2, 106.3, 59.4, 45.5, 41.6, 32.8, 27.3, 23.3, 21.3, 20.6, 14.3. MS (ESI-QTOF) for $C_{14}H_{27}N_5$ $[M+H]^+$ calculated 266.2339, found 266.2370.

N$^4$-Butyl-5-(3-(diethylamino)propyl)-6-methylpyrimidine-2,4-diamine (45o)

Intermediate compound 44o. N,N-Diethylprop-2-yn-1-amine was used as reagent. Yellow solid (44 mg, 76%). MS (ESI-QTOF) for $C_{16}H_{27}N_5[M+H]^+$ calculated 290.2339, found 290.2320.

Compound 45o. White solid (20 mg, 68%). $^1$H NMR (500 MHz, MeOD) δ 3.41 (t, J=7.2 Hz, 2H), 2.67 (q, J=7.2 Hz, 4H), 2.60 (t, J=7.1 Hz, 2H), 2.42 (t, J=7.7 Hz, 2H), 2.19 (s, 3H), 1.66-1.55 (m, 4H), 1.42-1.34 (m, 2H), 1.09 (t, J=7.2 Hz, 6H), 0.96 (t, J=7.4 Hz, 3H). $^{13}$C NMR (126 MHz, MeOD) δ 163.3, 160.8, 158.7, 106.6, 52.8, 47.8, 41.7, 32.7, 26.0, 23.3, 21.3, 19.8, 14.3, 10.9. MS (ESI-QTOF) for $C_{16}H_{31}N_5[M+H]^+$ calculated 294.2652, found 294.2660.

tert-Butyl 4-(3-(2-amino-4-(butylamino)-6-methylpyrimidin-5-yl)propyl)piperazine-1-carboxylate (45p)

Intermediate compound 44p. tert-Butyl 4-(prop-2-yn-1-yl)piperazine-1-carboxylate was used as reagent. Yellow solid (60 mg, 75%). MS (ESI-QTOF) for $C_{21}H_{34}N_6O_2[M+H]^+$ calculated 403.2816, found 403.2780.

Compound 45p. White solid (30 mg, 74%). $^1$H NMR (500 MHz, MeOD) δ 3.47-3.41 (m, 4H), 3.39 (t, J=7.2 Hz, 2H), 2.46-2.35 (m, 8H), 2.17 (s, 3H), 1.69-1.63 (m, 2H), 1.61-1.54 (m, 2H), 1.46 (s, 9H), 1.41-1.34 (m, 2H), 0.96 (t, J=7.4 Hz, 3H). $^{13}$C NMR (126 MHz, MeOD) δ 163.4, 161.9, 161.1, 156.4, 106.3, 81.3, 58.3, 54.0 (2C), 41.5, 33.0, 28.6, 26.3, 23.2, 21.3, 20.5, 14.3. MS (ESI-QTOF) for $C_{21}H_{38}N_6O_2[M+H]^+$ calculated 407.3129, found 407.3152.

N$^4$-Butyl-6-methyl-5-(3-(piperazin-1-yl)propyl)pyrimidine-2,4-diamine trihydrochloride (45q)

To a stirred solution of N-Boc protected compound 45p (20.3 mg, 0.05 mmol) in 1,4-dioxane (1 mL) was added hydrogen chloride (1 mL, 4 M in dioxane), and the reaction mixture was stirred for 3 h at room temperature. Excess solvent was removed under reduced pressure and the resulted residue was thoroughly washed with diethyl ether to obtain the desired compound 45q as a white solid (16 mg, 77%). $^{1}$H NMR (500 MHz, MeOD) δ 3.92-3.82 (m, 2H), 3.75-3.64 (m, 4H), 3.56-3.47 (m, 4H), 3.41 (t, J=7.5 Hz, 2H), 2.59 (t, J=8.0 Hz, 2H), 2.34 (s, 3H), 1.99-1.91 (m, 2H), 1.70-1.60 (m, 2H), 1.44-1.33 (m, 2H), 0.96 (t, J=7.4 Hz, 3H). $^{13}$C NMR (126 MHz, MeOD) δ 163.4, 155.8, 149.6, 106.9, 57.5, 49.8, 42.3, 42.0, 32.2, 23.5, 22.3, 21.2, 16.7, 14.2. MS (ESI-QTOF) for $C_{16}H_{30}N_{6}$ [M+H]$^{+}$ calculated 307.2605, found 307.2632.

Compounds 45r-w were synthesized similarly as compound 39a.

$N^{4}$-Butyl-6-methyl-5-(3-(4-methylpiperazin-1-yl)propyl)pyrimidine-2,4-diamine (45r)

Intermediate compound 44r. 1-Methyl-4-(prop-2-yn-1-yl)piperazine was used as reagent. Pale yellow solid (45 mg, 71%). MS (ESI-QTOF) for $C_{17}H_{28}N_{6}$[M+H]$^{+}$ calculated 317.2448, found 317.2445.

Compound 45r. White solid (22 mg, 69%). $^{1}$H NMR (500 MHz, CDCl$_{3}$) δ 6.74 (s, 1H), 4.81 (s, 2H), 3.43-3.35 (m, 2H), 2.69-2.25 (m, 15H), 2.22 (s, 3H), 1.71-1.65 (m, 2H), 1.59-1.53 (m, 2H), 1.42-1.34 (m, 2H), 0.95 (t, J=7.3 Hz, 3H). $^{13}$C NMR (126 MHz, CDCl$_{3}$) δ 162.9, 161.5, 160.6, 105.4, 55.6, 55.4, 52.9, 46.3, 40.7, 32.5, 25.5, 21.7, 21.2, 20.4, 14.1. MS (ESI-QTOF) for $C_{17}H_{32}N^{6}$ [M+H]$^{+}$ calculated 321.2761, found 321.2795.

$N^{4}$-Butyl-6-methyl-5-(3-(4-phenylpiperazin-1-yl)propyl)pyrimidine-2,4-diamine (45s)

Intermediate compound 44s. 1-Phenyl-4-(prop-2-yn-1-yl)piperazine was used as reagent. Pale yellow solid (57 mg, 75%). MS (ESI-QTOF) for $C_{22}H_{30}N_{6}$[M+H]$^{+}$ calculated 379.2605, found 379.2598.

Compound 45s. Pale oil (26 mg, 68%). $^{1}$H NMR (500 MHz, MeOD) δ 7.25-7.22 (m, 2H), 6.99-6.96 (m, 2H), 6.86-6.83 (m, 1H), 3.44 (t, J=7.2 Hz, 2H), 3.20 (t, J=5.0 Hz, 4H), 2.65 (t, J=5.0 Hz, 4H), 2.50-2.41 (m, 4H), 2.22 (s, 3H), 1.76-1.66 (m, 2H), 1.64-1.54 (m, 2H), 1.42-1.34 (m, 2H), 0.95 (t, J=7.4 Hz, 3H). $^{13}$C NMR (126 MHz, MeOD) δ 163.6, 160.0, 157.4, 152.6, 130.1, 121.3, 117.5, 107.0, 58.1, 54.2, 50.4, 41.7, 32.8, 26.2, 23.0, 21.2, 19.3, 14.3. MS (ESI-QTOF) for $C_{22}H_{34}N_{6}$ [M+H]$^{+}$ calculated 383.2918. found 383.2944.

$N^{4}$-Butyl-6-methyl-5-(3-thiomorpholinopropyl)pyrimidine-2,4-diamine (45t)

Intermediate compound 44t. 4-(Prop-2-yn-1-yl)thiomorpholine was used as reagent. Pale yellow solid (40 mg, 63%). MS (ESI-QTOF) for $C_{16}H_{25}N_{5}S$ [M+H]$^{+}$ calculated 320.1903, found 320.1880.

Compound 45t. White solid (25 mg, 77%). $^{1}$H NMR (500 MHz, MeOD) δ 3.40 (t, J=7.2 Hz, 2H), 2.74-2.71 (m, 4H), 2.69-2.66 (m, 4H), 2.42-2.38 (m, 2H), 2.17 (s, 3H), 1.69-1.53 (m, 4H), 1.44-1.33 (m, 2H), 0.96 (t, J=7.4 Hz, 3H). $^{13}$C NMR (126 MHz, MeOD) δ 163.3, 161.6, 160.4, 106.5, 59.0, 56.2, 41.6, 32.9, 28.3, 26.0, 23.2, 21.3, 20.3, 14.3. MS (ESI-QTOF) for $C_{16}H_{29}N_{5}S$ [M+H]$^{+}$ calculated 324.2216, found 324.2247.

$N^{4}$-Butyl-6-methyl-5-(3-morpholinopropyl)pyrimidine-2,4-diamine (45u)

Intermediate compound 44u. 4-(Prop-2-yn-1-yl)morpholine was used as reagent. Yellow solid (50 mg, 82%). $^{1}$H NMR (500 MHz, CDCl$_{3}$) δ 5.33 (s, 1H), 4.85 (s, 2H), 3.76 (t, J=4.6 Hz, 4H), 3.59 (s, 2H), 3.45-3.36 (m, 2H), 2.62 (t, J=4.6 Hz, 4H), 2.33 (s, 3H), 1.61-1.51 (m, 2H), 1.45-1.33 (m, 2H), 0.95 (t, J=7.4 Hz, 3H). $^{13}$C NMR (126 MHz, CDCl$_{3}$) δ 167.5, 163.1, 160.8, 93.7, 91.1, 79.3, 67.0, 52.5, 48.6, 40.6, 31.9, 23.1, 20.2, 14.0. MS (ESI-QTOF) for $C_{16}H_{25}N_{5}O$ [M+H]$^{+}$ calculated 304.2132, found 304.2147.

Compound 45u. White solid (24 mg, 78%). $^{1}$H NMR (500 MHz, CDCl$_{3}$) δ 6.45 (s, 1H), 4.79 (s, 2H), 3.76-3.74 (m, 4H), 3.40-3.36 (m, 2H), 2.47-2.41 (m, 4H), 2.39 (t, J=6.7 Hz, 2H), 2.28 (t, J=6.4 Hz, 2H), 2.22 (s, 3H), 1.73-1.63 (m, 2H), 1.60-1.50 (m, 2H), 1.43-1.32 (m, 2H), 0.94 (t, J=7.3 Hz, 3H). $^{13}$C NMR (126 MHz, CDCl$_{3}$) 162.8, 160.1, 159.9, 105.4, 67.1, 56.2, 53.5, 40.9, 32.4, 25.0, 21.6, 20.6, 20.4, 14.1. MS (ESI-QTOF) for $C_{16}H_{29}N_{5}O$ [M+H]$^{+}$ calculated 308.2445, found 308.2472.

$N^{4}$-Butyl-5-(3-((2-methoxyethyl)(methyl)amino)propyl)-6-methylpyrimidine-2,4-diamine (45v)

Intermediate compound 44v. N-(2-Methoxyethyl)-N-methylprop-2-yn-1-amine was used as reagent. Brownish oil (50 mg, 82%). MS (ESI-QTOF) for $C_{16}H_{27}N_{5}O$ [M+H]$^{+}$ calculated 306.2288, found 306.2275.

Compound 45v. Pale oil (24 mg, 77%). $^{1}$H NMR (500 MHz, MeOD) δ 3.52 (t, J=5.5 Hz, 2H), 3.38 (t, J=7.2 Hz, 2H), 3.34 (s, 3H), 2.59 (t, J=5.5 Hz, 2H), 2.44-2.39 (m, 4H), 2.26 (s, 3H), 2.16 (s, 3H), 1.67-1.53 (m, 4H), 1.45-1.33 (m, 2H), 0.96 (t, J=7.4 Hz, 3H). $^{13}$C NMR (126 MHz, MeOD) δ 163.4, 162.0, 161.1, 106.5, 71.4, 59.0, 57.8, 57.1, 43.1, 41.7, 32.9, 26.8, 23.3, 21.3, 20.5, 14.3. MS (ESI-QTOF) for $C_{16}H_{31}N_{5}O$ [M+H]$^{+}$ calculated 310.2601, found 310.2608.

$N^{4}$-Butyl-6-methyl-5-(4-morpholinobutyl)pyrimidine-2,4-diamine (45w)

Intermediate compound 44w. 4-(But-3-yn-1-yl)morpholine was used as reagent. Yellow solid (48 mg, 76%). MS (ESI-QTOF) for $C_{17}H_{27}N_{5}O$ [M+H]$^{+}$ calculated 318.2288, found 318.2324.

Compound 45w. White solid (25 mg, 78%). $^{1}$H NMR (500 MHz, MeOD) δ 3.71-3.68 (m, 4H), 3.38 (t, J=7.2 Hz, 2H), 2.47-2.45 (m, 4H), 2.43-2.36 (m, 4H), 2.16 (s, 3H), 1.64-1.52 (m, 4H), 1.49-1.32 (m, 4H), 0.95 (t, J=7.4 Hz, 3H). $^{13}$C NMR (126 MHz, MeOD) δ 163.0, 162.0, 161.0, 106.8, 67.6, 59.9, 54.8, 41.5, 32.9, 27.4, 26.9, 25.6, 21.3, 20.6, 14.3. MS (ESI-QTOF) for $C17H_{31}N_{5}O$ [M+H]$^{+}$ calculated 322.2601, found 322.2601.

Human TLR7/8-Specific Reporter Gene Assays (NF-kB Induction), and TLR-2/-3/-4/-5/-9 Counter-Screens:

The induction of NF-kB was quantified using human TLR-2/-3/-4/-5/-7/-8/-9-specific, rapid-throughput, liquid handler-assisted reporter gene assays as previously described by us.[31,32,47,48] HEK293 cells stably co-transfected with the appropriate hTLR and secreted alkaline phosphatase (sAP) were maintained in HEK-Blue™ Selection medium. Stable expression of secreted alkaline phosphatase (sAP) under control of NF-kB/AP-1 promoters is inducible by appropriate TLR agonists, and extracellular sAP in the supernatant is proportional to NF-kB induction. Reporter cells were incubated at a density of ~10$^{5}$ cells/ml in a volume of 80 μl/well, in 384-well, flat-bottomed, cell culture-treated microtiter plates in the presence of graded concentrations of stimuli, sAP was assayed spectrophotometrically using an alkaline phosphatase-specific chromogen (present in HEK-detection medium as supplied by InvivoGen) at 620 nm.

Multiplexed Immunoassays for Cytokines.

Fresh human peripheral blood mononuclear cells (hPBMC) were isolated from human blood obtained by venipuncture in Cell Preparation Tubes (CPT, Beckton-Dickinson) with informed consent and as per guidelines approved by the University of Minnesota Human Subjects Experimentation Committee. Aliquots of PBMCs ($10^5$ cells in 100 mL/well) were stimulated for 16 h with graded concentrations of test compounds. Supernatants were isolated by centrifugation, and were assayed in duplicates using analyte-specific multiplexed cytokine/chemokine bead array assays (HCYTMAG-60K-PX41 MILLIPLEX MAP Human Cytokine/Chemokine Magnetic Bead Panel, EMD Millipore, Billerica, Mass.) as reported by us previously.[42] The following analytes were quantified: sCD40L, VEGF, TNF-β, TNF-α, TGF-α, RANTES, PDGF-AB/BB, PDGF-AA, MIP-1β, MIP-1α, MDC (CCL22), MCP-3, MCP-1, IP-10, IL-17A, IL-15, IL-13, IL-12 (p70), IL-12 (p40), IL-10, IL-9, IL-8, IL-7, IL-6, IL-5, IL-4, IL-3, IL-2, IL-1ra, IL-1, IL-1α, IFN-γ, IFN-α2, GRO, GM-CSF, G-CSF, fractalkine, Fit-3 ligand, FGF-2, eotaxin, EGF.

IFN-α/β, IFN-γ, and TNF-α/IL-1β Whole Blood Reporter Gene Assays.

Whole heparinized blood was collected from consenting subjects as approved by the University of Minnesota Institutional Review Board, and was diluted 1:2 in RPMI supplemented with 10% fetal bovine serum (FBS). Forty μL was added to 384-well, flat-bottomed, cell culture-treated microtiter plates containing serial dilutions of compounds. Following incubation at 37° C. for 24 h, 40 μL of supernatant was transferred to separate 384-well plates using liquid handler equipped with liquid level sensing in order to avoid disturbing the erythrocyte-rich pellet. Forty μL of HEK-IFNα/β, HEK-IFNγ, or HEK-TNFα/IL-1β cytokine reporter cells (InvivoGen, San Diego, Calif.) harvested at a density of $1\times10^6$ cells/mL in DMEM with 10% FBS were added to the supernatant plates and incubated at 37° C. for 24 hours. The plates were washed in sterile PBS using a plate washer (BioTek, Winooski, Vt.), and 40 μL of HEK Blue Detection Media (InvivoGen, San Diego, Calif.) was added and incubated for 16 hours at 37° C. sAP was assayed spectrophotometrically using an alkaline phosphatase-specific chromogen (present in HEK-detection medium as supplied by InvivoGen) at 620 nm.

In order to calibrate the assays, human serum (or plasma) was 'spiked' with graded concentrations of human IFN-α, IFN-γ, or TNF-α, and cytokine reporter assays were performed as described above. Sigmoidal dose-response profiles for each cytokine were observed (FIG. 4 and FIG. S3), from which threshold cytokine concentrations corresponding to maximal responses for each cytokine reporter cell line were recorded. Compound concentrations eliciting maximal cytokine responses were defined as Effective Concentrations eliciting Maximal Responses ($ECMR_{100}$).

Flow-Cytometric Immunostimulation Experiments:

Cell surface marker upregulation was determined by flow cytometry using protocols published by us previously[64] and modified for rapid throughput. Briefly, PBMC samples were obtained by venipuncture in CPT Vacutainer tubes (Becton-Dickinson Biosciences, San Jose, Calif.) from healthy human volunteers with informed consent and as per guidelines approved by the University of Minnesota Institutional Review Board. Serial dilutions of selected compounds were performed using a Bio-Tek Precision 2000 XS liquid handler in sterile 96-well polypropylene plates, to which 100 μL aliquots of PBMCs were added. The plates were incubated at 37° C. for 16 h. Negative (DMSO) controls were included in each experiment. The following fluorochrome-conjugated antibodies were used for pDCs: CD11c PerCP-Cy5.5 (BioLegend, San Diego, Calif.), CD304 BV421, CD123 BV510, Lin Cocktail FITC, CD80 PE, HLA-DR APC (Becton-Dickinson Biosciences, San Jose, Calif.) and Fixable Viability Dye eFluor 780 (eBioscience, San Diego, Calif.), and for cDCs: CD1c BV421, CD141 BV510, Lin Cocktail FITC, CD80 PE, CD11c PerCP-Cy5.5, HLA-DR APC (Becton-Dickinson Biosciences, San Jose, Calif.) and Fixable Viability Dye eFluor 780 (eBioscience, San Diego, Calif.). Following incubation, PBMCs were washed with sterile PBS and stained with 1:1000 eFluor780 in PBS for 20 min at 4° C. Viability staining was followed by washing with RPMI containing 10% FBS and 2.5 μg of each antibody was added to wells with a liquid handler and incubated at 4° C. in the dark for 30 min. Following staining PBMCs were fixed by mixing 200 μL of the samples in 800 μL prewarmed cytofix buffer (Becton-Dickinson Biosciences, San Jose, Calif.) in 96 deep-well plates. After washing the cells twice at 300 g for 10 min in RPMI, the cells were transferred to a 96-well plate. Flow cytometry was performed using a BD FACSVerse instrument for acquisition on 250,000 gated events. Compensation for spillover was computed for each experiment on singly stained UltraComp Beads (eBioscience, San Diego, Calif.). Fluorescence minus one (FMO) and isotype controls were used to identify DC populations.[69-71] pDCs were defined as Live, Lin$^-$, CD123$^+$, CD303$^+$, CD304$^+$, HLA-DR$^+$. CD141$^+$ cDCs were defined as Live, Lin$^-$, CD1c$^-$, CD141$^+$, HLA-DR$^+$. CD1c$^+$ cDC were defined as Live, Lin$^-$, CD141$^-$, CD1c$^+$, CD11c$^+$, HLA-DR$^+$. Median fluorescence intensities were quantified for each population using FlowJo, version 10.0, software (FlowJo, LLC, Ashland, Oreg.).

Statistical Methods:

Data were analyzed and plotted using Origin Version 7 (OrginLab, Northampton, Mass.). P values for regression coefficients denote significance levels (two-tailed) for the t-test of the slope=0.

Abbreviations:

APCs, Antigen-presenting cells; CD, Cluster of differentiation; cDC, conventional dendritic cell; DIPEA, N,N-diisopropylethylamine; $ECMR_{100}$, Effective Concentrations eliciting Maximal Responses; ESI-QTOF, Electrospray ionization-quadrupole time of flight; $EC_{50}$, Half-maximal effective concentration; HEK, Human embryonic kidney; HLA-DR, Human Leukocyte Antigen-antigen D Related; IFN, Interferon; IL, Interleukin; MPLA, monophosphoryl lipid A; NIS, N-iodosuccinimide; mDC, myeloid dendritic cell; PAMPs, pathogen-associated molecular patterns; PBMCs, Peripheral blood mononuclear cells; pDC, plasmacytoid dendritic cell; NF-kB, Nuclear factor-kB; PRRs, pattern-recognition receptors; sAP, Secreted alkaline phosphatase; Th1, Helper T lymphocyte-type 1; Th2, Helper T lymphocyte-type 2; Th9, Helper T lymphocyte-type 9; Th17, Helper T lymphocyte-type 17; TLR, Toll-like receptor; TNF-a, Tumor necrosis factor-a.

What is claimed is:

1. A compound of the Formula (II):

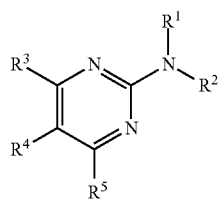

(II)

or a pharmaceutically acceptable salt or solvate thereof, wherein:

R¹ and R² are each, independently, H, $(C_1-C_{20})$-alkyl or $(C_6-C_{20})$-aryl-$(C_1-C_{20})$-alkyl;

R³ is $(C_1-C_{20})$-alkyl, or $(C_6-C_{12})$--aryl;

R⁴ is $(C_{1-20})$-alkyl-NR⁶R⁷, wherein R⁶ and R⁷, together with the nitrogen to which they are attached from a $(C_2-C_{20})$-heterocyclyl group; and R⁵ is NR⁸R⁹, wherein R⁸ and R⁹ are each, independently, H, $(C_{1-20})$- alkyl or $(C_{6-12})$-aryl-$(C_{1-20})$-alkyl.

2. The compound of claim 1 or a pharmaceutically acceptable salt or solvate thereof, wherein the $(C_2-C_{20})$-heterocyclyl group is a $(C_2-C_6)$-heterocyclyl group or a $(C_2-C_4)$-heterocyclyl group.

3. The compound of claim 1 or a pharmaceutically acceptable salt or solvate thereof, wherein:

R³ is $(C_1-C_{20})$-alkyl.

4. A compound of the formula:

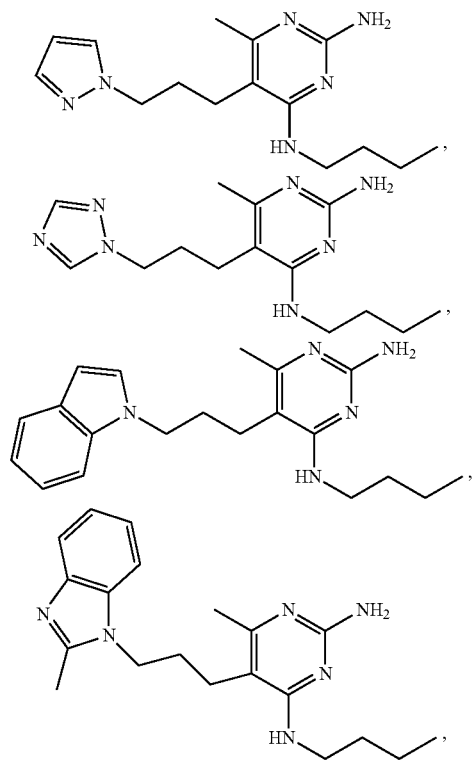

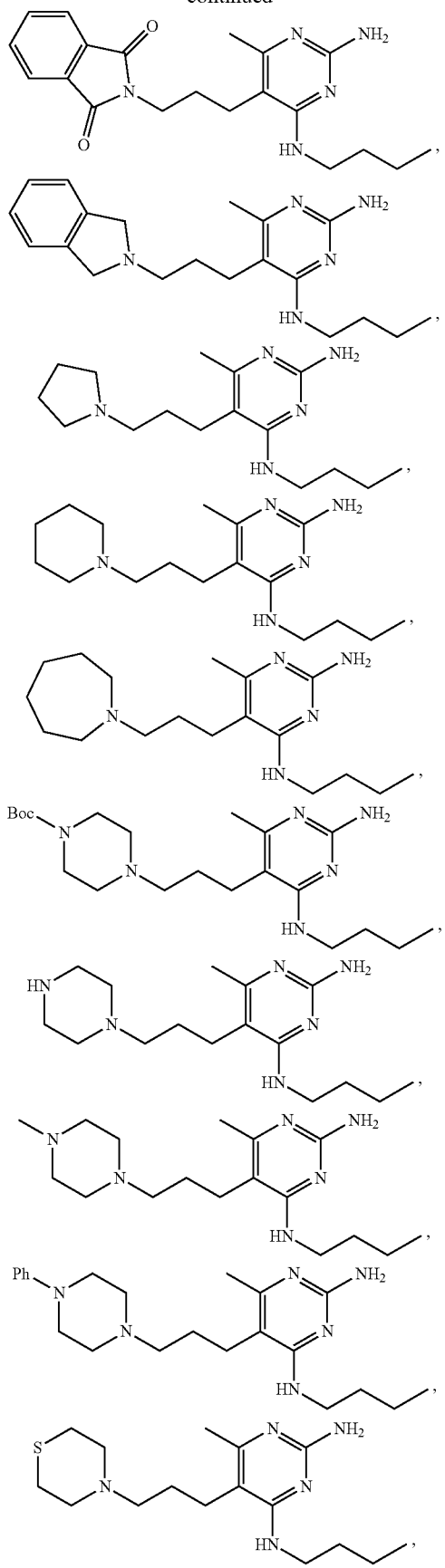

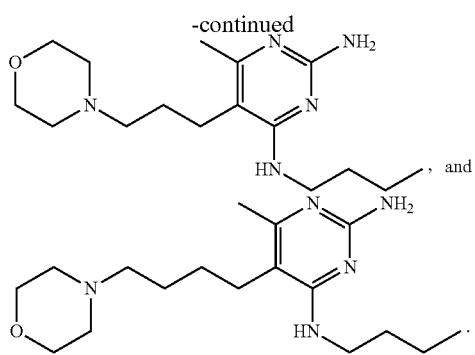

or a pharmaceutically acceptable salt or solvate thereof.

5. A pharmaceutical compositions comprising one or more compounds of claim 1 or a pharmaceutically acceptable salt or solvate thereof and a pharmaceutically acceptable carrier.

6. A method of inhibiting an immune response in a subject, the method comprising administering to the subject an amount of a compound of claim 1 or a pharmaceutically acceptable salt or solvate thereof, effective to inhibit the immune response in the subject.

7. The method wherein the immune response is associated with an autoimmune disease.

8. The method of claim 6, wherein inhibiting the immune response ameliorates one or more symptoms of the autoimmune disease.

9. The method of claim 8 wherein the autoimmune disease is selected from the group consisting of rheumatoid arthritis, pancreatitis, mixed tissue connective disease, systemic lupus erythematosus, antiphospholipid syndrome, irritable bowel disease, type I diabetes mellitus, and Sjogren's disease.

10. The method of claim 9, wherein the autoimmune disease is Sjogren's disease.

* * * * *

UNITED STATES PATENT AND TRADEMARK OFFICE
CERTIFICATE OF CORRECTION

| | |
|---|---|
| PATENT NO. | : 10,662,161 B2 |
| APPLICATION NO. | : 15/879826 |
| DATED | : May 26, 2020 |
| INVENTOR(S) | : David et al. |

It is certified that error appears in the above-identified patent and that said Letters Patent is hereby corrected as shown below:

In the Specification

In Column 18, Line 38, delete "carded" and insert --carried-- therefor

In Column 25, Line 9, delete "5-iodo-6-methyl-M-propylpyrimidine-2,4-diamine" and insert --5-Iodo-6-methyl-$N^4$-propylpyrimidine-2,4-diamine-- therefor In Column 25, Line 17, delete "$C_8H_3IN_4$" and insert --$C_8H_{13}IN_4$-- therefor In Column 25, Line 20, delete "5-iodo-6-methyl-$N^4$-pentylpyrimidine-2,4-diamine" and insert --5-Iodo-6-methyl-$N^4$-pentylpyrimidine-2,4-diamine-- therefor In Column 25, Line 26, before "166.66,", insert --δ--

In Column 26, Line 51, delete "b" and insert --δ-- therefor

In Column 27, Line 8, delete "5-iodo-4-methyl-6-pentylpyrimidin-2-amine" and insert --5-Iodo-4-methyl-6-pentylpyrimidin-2-amine-- therefor In Column 27, Line 66, delete "$C_9H_5BrN_4$" and insert --$C_9H_{15}BrN_4$-- therefor In Column 28, Line 58, delete "$C_9H_{14}N_4$" and insert --$C_9H_{16}N_4$-- therefor In Column 30, Line 12, delete "5-Benzyl-MN-butyl-6-methylpyrimidine-2,4-diamine" and insert --5-Benzyl-$N^4$-butyl-6-methylpyrimidine-2,4-diamine-- therefor In Column 31, Line 6, delete "$C_{12}H_2N_5$" and insert --$C_{12}H_{23}N_5$-- therefor In Column 31, Lines 11-12, delete "5-(4-Aminobutyl)-N-butyl-6-methylpyrimidine-2,4-diamine" and insert --5-(4-Aminobutyl)-$N^4$-butyl-6-methylpyrimidine-2,4-diamine-- therefor Signed and Sealed this
Thirteenth Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,662,161 B2

In Column 31, Lines 29-30, delete "5-(5-Aminopentyl)-MN-butyl-6-methylpyrimidine-2,4-diamine" and insert --5-(5-Aminopentyl)-$N^4$-butyl-6-methylpyrimidine-2,4-diamine-- therefor In Column 32, Line 11, delete "5167.91," and insert --δ 167.91,-- therefor In Column 32, Lines 17-18, delete "5-(3-Aminopropyl)-M-butyl-6-phenylpyrimidine-2,4-diamine" and insert --5-(3-Aminopropyl)-$N^4$-butyl-6-phenylpyrimidine-2,4-diamine-- therefor In Column 33, Line 40, delete "TNF-α." and insert --TNF-α,-- therefor In Column 33, Line 42, delete "(p40)." and insert --(p40),-- therefor In Column 33, Line 43, delete "IL-1 ra," and insert --IL-1ra,-- therefor In Column 34, Line 23, delete "(M-hexyl)," and insert --($N^4$-hexyl),-- therefor In Column 41, Line 54, delete "C9H$_{14}$ClN$_3$" and insert --$C_9H_{14}ClN_3$-- therefor In Column 42, Line 29, delete "C$_8$H$_{15}$IN$_4$" and insert --$C_9H_{15}IN_4$-- therefor In Column 43, Line 16, delete "C13H$_{24}$N$_4$O" and insert --$C_{13}H_{24}N_4O$-- therefor In Column 43, Line 24, delete "Cl$_4$H$_{22}$N$_4$O" and insert --$C_{14}H_{22}N_4O$-- therefor In Column 45, Line 23, delete "C$_{19}$H$_2$N$_4$" and insert --$C_{19}H_{28}N_4$-- therefor In Column 45, Line 51, delete "MHz." and insert --MHz,-- therefor In Column 45, Line 51, delete "b" and insert --δ-- therefor In Column 46, Lines 9-10, delete "5-(3-(1H-1,2,4-Triazol-1-yl)propyl)-M-butyl-6-methylpyrimidine-2,4-diamine" and insert --5-(3-(1*H*-1,2,4-Triazol-1-yl)propyl)-$N^4$-butyl-6-methylpyrimidine-2,4-diamine-- therefor In Column 46, Lines 25-26, delete "5-(3-(1H-Indol-1-yl)propyl)-M-butyl-6-methylpyrimidine-2,4-diamine" and insert --5-(3-(1*H*-Indol-1-yl)propyl)-$N^4$-butyl-6-methylpyrimidine-2,4-diamine-- therefor In Column 46, Line 38, delete "5161.2," and insert --δ 161.2,-- therefor In Column 47, Lines 10-11, delete "N$^4$-Butyl-5-(3-(Isoindolin-2-yl)propyl)-6-methylpyrimidine-2,4-diamine (45)" and insert --$N^4$-Butyl-5-(3-(isoindolin-2-yl)propyl)-6-methylpyrimidine-2,4-diamine (45j)-- therefor In Column 47, Line 53, delete "MHz." and insert --MHz,-- therefor In Column 47, Lines 61-62, delete "5-(3-(Azepan-1-yl)propyl)-M-butyl-6-methylpyrimidine-2,4-diamine" and insert --5-(3-(Azepan-1-yl)propyl)-$N^4$-butyl-6-methylpyrimidine-2,4-diamine-- therefor In Column 48, Line 5, before "163.0,", insert --δ--

In Column 49, Line 26, delete "$C_{17}H_{32}N^6$" and insert --$C_{17}H_{32}N_6$-- therefor In Column 49, Line 44, delete "383.2918." and insert --383.2918,-- therefor In Column 50, Line 13, before "162.8,", insert --δ--

In Column 50, Line 47, delete "C17H$_{31}$N$_5$O" and insert --$C_{17}H_{31}N_5O$-- therefor In Column 50, Line 64, delete "stimuli," and insert --stimuli.-- therefor In Column 51, Line 54, delete "(FIG. 4 and FIG. S3)," and insert --(FIG. 4),-- therefor In Column 52, Line 20, delete "eFluor780" and insert --eFluor 780-- therefor In the Claims In Column 53, Line 20, in Claim 1, delete "($C_1$-$C_{20}$)-alkyl," and insert --($C_1$-$C_{20}$)-alkyl-- therefor In Column 53, Line 26, in Claim 1, delete "(C1-20)- alkyl" and insert --($C_{1-20}$)-alkyl-- therefor In Column 54, Lines 41-47, in Claim 4, delete " 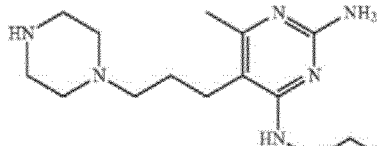 " and insert

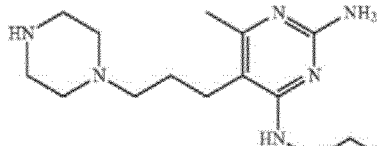

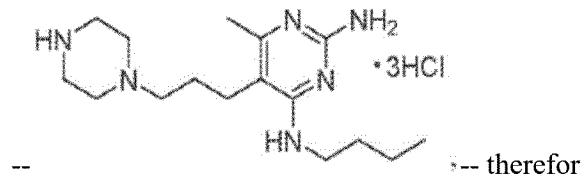

-- --- therefor

In Column 56, Line 6, in Claim 7, after "method", insert --of claim 6,--

In Column 56, Line 11, in Claim 9, after "claim 8", insert --,--